United States Patent
Fuchiwaki et al.

(10) Patent No.: US 12,289,991 B2
(45) Date of Patent: *Apr. 29, 2025

(54) ORGANIC ELECTROLUMINESCENCE DEVICE

(71) Applicant: SAMSUNG DISPLAY CO., LTD., Yongin-si (KR)

(72) Inventors: Junta Fuchiwaki, Yokohama (JP); Ikuo Sasaki, Yokohama (JP); Shuri Sato, Yokohama (JP); Nobutaka Akashi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 717 days.

This patent is subject to a terminal disclaimer.

(21) Appl. No.: 15/860,857

(22) Filed: Jan. 3, 2018

(65) Prior Publication Data

US 2018/0205019 A1    Jul. 19, 2018

(30) Foreign Application Priority Data

Jan. 19, 2017    (KR) .................. 10-2017-0009344

(51) Int. Cl.
*H10K 85/60*    (2023.01)
*C07D 401/10*    (2006.01)
(Continued)

(52) U.S. Cl.
CPC ......... *H10K 85/654* (2023.02); *C07D 401/10* (2013.01); *C07D 401/14* (2013.01);
(Continued)

(58) Field of Classification Search
None
See application file for complete search history.

(56) References Cited

U.S. PATENT DOCUMENTS 7,714,149 B2    5/2010    Zhang
8,632,893 B2    1/2014    Lin et al.
(Continued)

FOREIGN PATENT DOCUMENTS

| CN | 105859714 A | 8/2016 |
| CN | 106328816 A | 1/2017 |

(Continued)

OTHER PUBLICATIONS

Nasu et al., a highly luminescent spiro-anthracenone-based organic light-emitting diode exhibiting thermally activated delayed fluorescence, Chem. Commun. 2013, vol. 49, p. 10385-10387, Sep. 27, 2013 (Year: 2013).*

(Continued)

*Primary Examiner* — Seokmin Jeon
(74) *Attorney, Agent, or Firm* — Womble Bond Dickinson (US) LLP

(57) ABSTRACT

An organic electroluminescence device including a first electrode, a hole transport region on the first electrode, an emission layer on the hole transport region, an electron transport region on the emission layer, and a second electrode on the electron transport region, wherein the hole transport region includes a first heterocyclic compound including 1 to 3 structures derived from a compound represented by Formula 1 below, and the emission layer
(Continued)

includes a second heterocyclic compound including 1 or 2 structures derived from a compound represented by Formula 1.

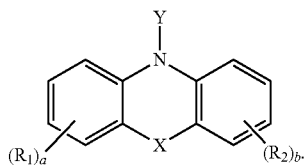

[Formula 1]

8 Claims, 2 Drawing Sheets

(51) Int. Cl.
    *C07D 401/14*     (2006.01)
    *C07D 413/14*     (2006.01)
    *C07D 417/14*     (2006.01)
    *H10K 50/11*     (2023.01)
    *H10K 50/18*     (2023.01)
    *H10K 85/40*     (2023.01)

(52) U.S. Cl.
    CPC ......... *C07D 413/14* (2013.01); *C07D 417/14* (2013.01); *H10K 85/40* (2023.02); *H10K 85/631* (2023.02); *H10K 50/11* (2023.02); *H10K 50/18* (2023.02)

(56) References Cited

U.S. PATENT DOCUMENTS

| | | | |
|---|---|---|---|
| 8,927,749 | B2 | 1/2015 | Boudreault et al. |
| 10,224,488 | B2 | 3/2019 | Yen et al. |
| 10,505,128 | B2 | 12/2019 | Chung et al. |
| 10,522,760 | B2* | 12/2019 | Fuchiwaki .......... H01L 51/0035 |
| 10,673,000 | B2* | 6/2020 | Fuchiwaki .......... H01L 51/0094 |
| 11,437,582 | B2 | 9/2022 | Duan et al. |
| 2002/0121860 | A1* | 9/2002 | Seo ............................... 313/506 |
| 2010/0104978 | A1 | 4/2010 | Sawano et al. |
| 2010/0171417 | A1* | 7/2010 | Kitamura ...................... 313/504 |
| 2010/0219406 | A1* | 9/2010 | Kahle ............................ 257/40 |
| 2011/0101319 | A1* | 5/2011 | Fukumatsu .................... 257/40 |
| 2012/0001537 | A1* | 1/2012 | Lin ................................ 313/504 |
| 2012/0074395 | A1* | 3/2012 | Yabunouchi ............ H01L 51/54 257/40 |
| 2012/0205640 | A1* | 8/2012 | Kai ........................ H01L 51/54 257/40 |
| 2013/0299811 | A1* | 11/2013 | Seki ........................ H01L 51/52 257/40 |
| 2014/0121293 | A1* | 5/2014 | Nakamura ............. C08G 75/08 |
| 2014/0138670 | A1* | 5/2014 | Nakagawa .......... H01L 51/0067 257/40 |
| 2014/0197393 | A1* | 7/2014 | Lee ................................ 257/40 |
| 2014/0306213 | A1* | 10/2014 | Sato .................... H01L 51/5275 257/40 |
| 2014/0316134 | A1* | 10/2014 | Stoessel .............. H01L 51/0054 544/180 |
| 2015/0188056 | A1* | 7/2015 | Suda .................... H01L 51/0069 |
| 2015/0228925 | A1* | 8/2015 | Chen ................... H01L 51/5253 |
| 2016/0093812 | A1 | 3/2016 | Stoessel et al. |
| 2016/0172600 | A1 | 6/2016 | Macdonald et al. |
| 2016/0372681 | A1 | 12/2016 | Parham et al. |
| 2017/0125701 | A1 | 5/2017 | Pfister et al. |
| 2017/0222147 | A1* | 8/2017 | Defranco ............ H01L 51/0016 |
| 2017/0263871 | A1* | 9/2017 | Wang ................... H01L 51/0072 |
| 2017/0346029 | A1* | 11/2017 | Kim ..................... H01L 51/5004 |
| 2018/0205019 | A1 | 7/2018 | Fuchiwaki et al. |
| 2020/0379353 | A1 | 12/2020 | Kaur et al. |

FOREIGN PATENT DOCUMENTS

| | | |
|---|---|---|
| JP | H08302339 A | 11/1996 |
| JP | 2002-265938 A | 9/2002 |
| JP | 2003-243178 A | 8/2003 |
| JP | 2004-253298 A | 9/2004 |
| JP | 2005-157259 A | 6/2005 |
| JP | 2016066631 A | 4/2016 |
| KR | 10-2006-0032930 A | 4/2006 |
| KR | 10-2009-0106562 A | 10/2009 |
| KR | 10-2011-0120075 A | 11/2011 |
| KR | 10-2015-0033700 A | 4/2015 |
| KR | 10-2015-0143552 A | 12/2015 |
| KR | 10-2016-0035062 A | 3/2016 |
| KR | 10-2016-0073914 A | 6/2016 |
| KR | 10-2017-0124012 A | 11/2017 |
| KR | 10-2020-0138007 A | 12/2020 |
| WO | WO 2007/110228 A1 | 10/2007 |
| WO | 2011/136484 A1 | 11/2011 |
| WO | WO 2013/083216 A1 | 6/2013 |
| WO | WO 2014/002629 A1 | 5/2016 |

OTHER PUBLICATIONS

The English translation of WO 2007/110228 A1 and the original WO 2007/110228 A1, Oct. 4, 2007 (Year: 2007).*
Wenzhi Zhang et al. "A new way towards high-efficiency thermally activated delayed fluorescence devices via external heavy-atom effect", Sci. Rep. 2016, vol. 6, p. 30178 (Year: 2016).*
Yunchuan Li et al. "Highly Efficient Spiro[fluorene-9,9'-thioxanthene] Core Derived Blue Emitters and Fluorescent/Phosphorescent Hybrid White Organic Light-Emitting Diodes" Chem. Mater. 2015, vol. 27, p. 1100-1109 (Year: 2015).*
Machine translated English version of WO 2016/116504 A1, David Ambrosek, Jul. 28, 2016 (Year: 2016).*
R. Grisorio et al. First disubstituted dibenzothiophene-5,5-dioxide monodispersed molecular materials for efficient blue-electroluminescence, J. Mater. Chem. 2010, vol. 20, p. 1012-1018 (Year: 2010).*
Giovanna Barbarella et al. "From easily oxidized to easily reduced thiophene-based materials" Adv. Mater. 1998, vol. 10, p. 551-554 (Year: 1998).*
Keiro Nasu et al. "A highly luminescent spiro-anthracenone-based organic light-emitting diode exhibiting thermally activated delayed fluorescence", Chem. Commun. 2013, vol. 49, p. 10385-10387 (Year: 2013).*
Pamela Schrogel et al. "A series of CBP-derivatives as host materials for blue phosphorescent organic light-emitting diodes" J. Mater. Chem. 2011, vol. 21, p. 2266-2273 (Year: 2011).*
Dongdong Zhang et al. "Sterically shielded blue thermally activated delayed fluorescence emitters with improved efficiency and stability", Mater. Horiz, 2016, vol. 3, p. 145-151 (Year: 2016).*
Silu Tao et al. "Efficient blue organic light-emitting devices based on novel anthracene derivatives with pronounced thermal stability and excellent film-forming property", Chem. Phys. Letts. 2006, vol. 429, p. 622-627 (Year: 2006).*
English translation of KR 2006/0032930 A and the original KR 2006/0032930 A, Jong Wook Park, Apr. 18, 2006 (Year: 2006).*
English translation of JP 2010/272618 A and the original JP 2010/272618 A, Masahito Nishizeki, Dec. 2, 202010 (Year: 2010).*
Peter Strohriegl et al. "Novel host materials for blue phosphorescent OLEDs" Proc. of SPIE 2013, vol. 8829, p. 882906-1 through-12 (Year: 2013).*
Huanhuan Li et al. "Efficient synthesis of p-extended phenazasilines for optical and electronic applications" Chem. Commun. 2014, vol. 50, p. 15760-15763 (Year: 2014).*
Shen Xu et al. "Efficient Synthesis of All-Aryl Phenazasilines for Optoelectronic Applications", Aust. J. Chem. 2016, vol. 69, p. 419-422 (Year: 2016).*
Hideki Hayashi et al. "Preparation and Properties of π-Conjugated Polymer with Phenazasiline Units", Chem. Letts. 2000, p. 688-689 (Year: 2000).*
Machine English Translation for corresponding Korean Patent Application No. 20110120075A, dated Nov. 3, 2011, 67 pages.

(56) References Cited

OTHER PUBLICATIONS

Machine English Translation for corresponding Korean Patent Application No. 10-2017-0124012 A, dated Nov. 9, 2017, 22 pages.
Office Action issued in U.S. Appl. No. 15/813,677 by the USPTO, dated Feb. 18, 2020, 12 pages.
Lin, et al., "High Energy Gap OLED Host Materials for Green and Blue PHOLED Materials," Journal of Display Technology, vol. 5, No. 6, pp. 236-240, Jun. 2009.
Machine translation of KR-20160073914, translation generated Apr. 2019, 35 pages. (Year: 2019).
Ito et al. "para-Phenylene-Bridged Spirobi(triarylamine) Dimer with Four Perpendicularly Linked Redox-Active Pi Systems" Chem. Eur. J. 2010, 16, 10866-10878. (Year: 2010).
Office Action dated May 3, 2019, issued in U.S. Appl. No. 15/684,112, 8 pages.
Korean Office Action dated Aug. 1, 2024, of the corresponding Korean Patent Application No. 10-2021-0086515 (6 pages).

* cited by examiner

ORGANIC ELECTROLUMINESCENCE DEVICE

CROSS-REFERENCE TO RELATED APPLICATIONS

Korean Patent Application No. 10-2017-0009344, filed on Jan. 19, 2017, in the Korean Intellectual Property Office, and entitled: "Organic Electroluminescence Device," is incorporated by reference herein in its entirety.

BACKGROUND

1. Field

Embodiments relate to an organic electroluminescence device.

2. Description of the Related Art

The development of an organic electroluminescence display as an image display is being actively conducted. The organic electroluminescence display is different from a liquid crystal display and is a self-luminescent display accomplishing display via the recombination of holes and electrons injected from a first electrode and a second electrode in an emission layer and via light emission from a luminescent material including an organic compound in the emission layer.

As an organic electroluminescence device, an organic device may include, e.g., a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state.

SUMMARY

Embodiments are directed to an organic electroluminescence device.

The embodiments may be realized by providing an organic electroluminescence device including a first electrode; a hole transport region on the first electrode; an emission layer on the hole transport region; an electron transport region on the emission layer; and a second electrode on the electron transport region, wherein the hole transport region includes a first heterocyclic compound including 1 to 3 structures derived from a compound represented by the following Formula 1, and the emission layer includes a second heterocyclic compound including 1 or 2 structures derived from a compound represented by Formula 1. The first electrode and the second electrode may each independently include at least one selected from Ag, Mg, Cu, Al, Pt. Pd, Au, Ni, Nd, Ir, Cr, Li, Ca, LiF/Ca, LiF/Al, Mo, Ti, In, Sn, and Zn, or a compound of two or more thereof, a mixture of two or more thereof, or an oxide thereof.

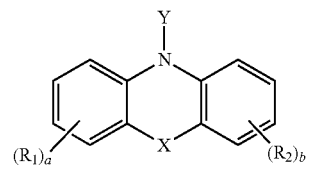

[Formula 1]

wherein, in Formula 1, X is O, S, $CR_wR_x$, or $SiR_yR_z$, Y, to $R_w$, $R_1$ and $R_2$ are each independently a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, Y, $R_w$ to $R_z$, $R_1$ and $R_2$ are separate or combined with an adjacent group to form a ring, and "a" and "b" are each independently an integer of 0 to 4.

The first heterocyclic compound may include 2 or 3 structures derived from the compound represented by Formula 1.

The first heterocyclic compound may include 2 structures derived from the compound represented by Formula 1, and the second heterocyclic compound may include 1 structure derived from the compound represented by Formula 1.

The first heterocyclic compound may be represented by the following Formula 2:

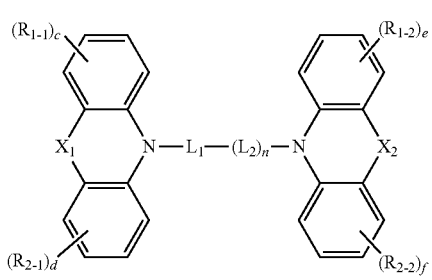

[Formula 2]

wherein, in Formula 2, $L_1$ and $L_2$ may be a substituted or unsubstituted arylene group having 6 to 30 ring carbon atoms or a substituted or unsubstituted heteroarylene group having 2 to 30 ring carbon atoms, "n" may be 0 or 1, $R_{1-1}$, $R_{1-2}$, $R_{2-1}$, and $R_{2-2}$ may be defined the same as $R_1$ and $R_2$ of Formula 1, "c" to "f" may be an integer of 0 to 4, and $X_1$ and $X_2$ may be defined the same as X of Formula 1.

$X_1$ and $X_2$ may be the same, $R_{1-1}$ and $R_{1-2}$ may be the same, $R_{2-1}$ and $R_{2-2}$ may be the same, "c" and "e" may be the same, and "d" and "f" may be the same.

The compound represented by Formula 2 may be represented by the following Formula 2-1:

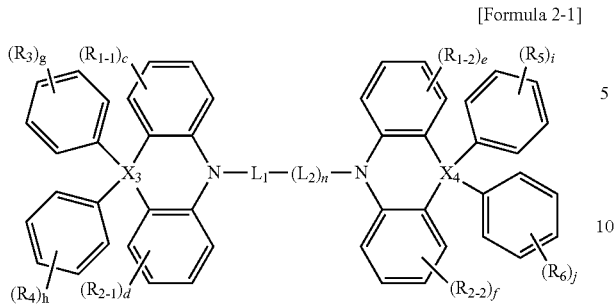

[Formula 2-1]

wherein, in Formula 2-1, $X_3$ and $X_4$ may be C or Si, $R_3$ to $R_6$ may be a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, "g" to "j" may be an integer of 0 to 5, $L_1$, $L_2$, $R_{1-1}$, $R_{1-2}$, $R_{2-1}$, $R_{2-2}$, "c" to "f", and "n" may be defined the same as those of Formula 2.

$X_3$ and $X_4$ may be the same.

The first heterocyclic compound may be represented by the following Formula 3:

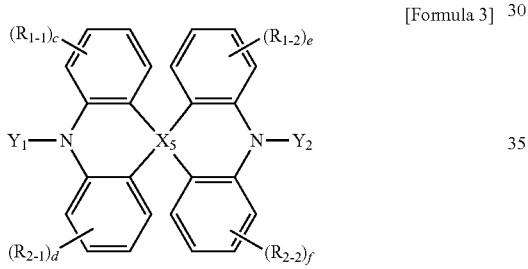

[Formula 3]

wherein, in Formula 3, $X_5$ may be C or Si, $Y_1$ and $Y_2$ may be defined the same as Y of Formula 1, $R_{1-1}$, $R_{1-2}$, $R_{2-1}$, and $R_{2-2}$ may be defined the same as $R_1$ and $R_2$ of Formula 1, and "c" to "f" may be an integer of 0 to 4.

The compound represented by Formula 3 may be represented by the following Formula 3-1:

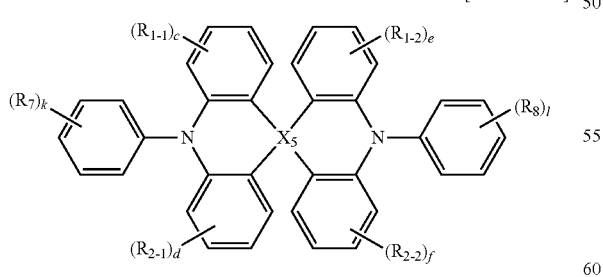

[Formula 3-1]

wherein, in Formula 3-1, $R_7$ and $R_8$ may be a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, "k" and "l" may be an integer of 0 to 5, and $X_5$, $R_{1-1}$, $R_{1-2}$, $R_{2-1}$, $R_{2-2}$, and "c" to "f" may be defined the same as those of Formula 3.

The compound represented by Formula 3 may be represented by the following Formula 3-2:

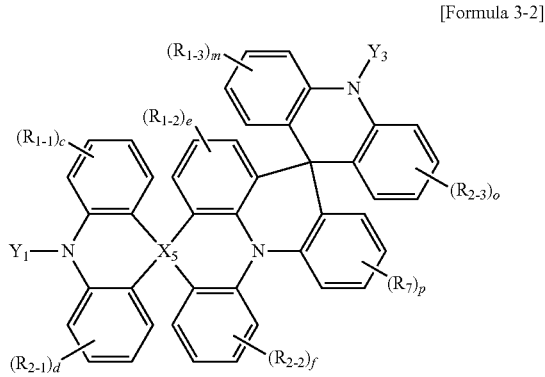

[Formula 3-2]

wherein, in Formula 3-2, $Y_3$ may be a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_{1-3}$, $R_{2-3}$ and $R_7$ may be a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_{1-3}$, $R_{2-3}$ and $R_7$ may be separate or may be combined with an adjacent group to form a ring, "e" may be an integer of 0 to 3, "m", "o," and "p" may be an integer of 0 to 4, and $X_5$, $Y_1$, $R_{1-1}$, $R_{1-2}$, $R_{2-1}$, $R_{2-2}$, "c", "d," and "f" may be defined the same as those of Formula 3.

The second heterocyclic compound may be represented by the following Formula 4:

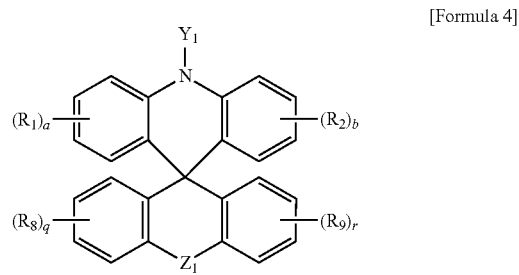

[Formula 4]

wherein, in Formula 4, $Z_1$ may be —CO—, or —SO$_2$—, $R_8$ and $R_9$ may be a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, "q" and "r" may be an integer of 0 to 4, $Y_1$ may be defined the same as Y of Formula 1, and $R_1$, $R_2$, "a" and "b" may be defined the same as those of Formula 1.

$Z_1$ may be —CO—.

The second heterocyclic compound may be represented by the following Formula 5:

[Formula 5]

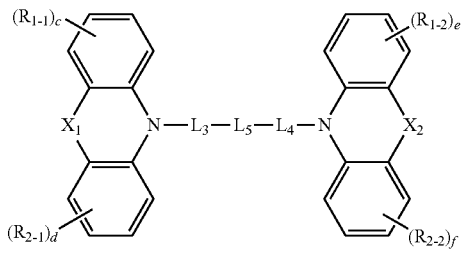

wherein, in Formula 5, $L_3$ and $L_4$ may be a substituted or unsubstituted arylene group having 6 to 30 ring carbon atoms or a substituted or unsubstituted heteroarylene group having 2 to 30 ring carbon atoms, $L_5$ may be —CO—, or —SO$_2$—, $R_{1-1}$, $R_{1-2}$, $R_{2-1}$, and $R_{2-2}$ may be defined the same as $R_1$ and $R_2$ of Formula 1, "c" to "l" may be an integer of 0 to 4, and $X_1$ and $X_2$ may be defined the same as X of Formula 1.

The second heterocyclic compound may be represented by the following Formula 6:

[Formula 6]

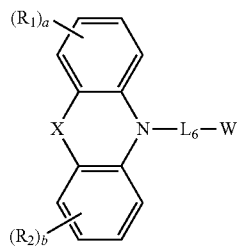

wherein, in Formula 6, X, $R_1$, $R_2$, "a," and "b" may be defined the same as those of Formula 1, $L_6$ may be a substituted or unsubstituted arylene group having 6 to 30 ring carbon atoms, and W may be a substituted or unsubstituted triazine group or a group represented by the following Formula 7:

[Formula 7]

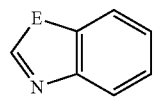

wherein in Formula 7, E may be O, S, or NR', R' may be a hydrogen atom, a deuterium atom, a substituted or unsubstituted alkyl group having 1 to 10 carbon atoms, or a substituted or unsubstituted aryl group having 6 to 30 ring carbon atoms.

The hole transport region may have a multilayer structure, and a layer adjacent to the emission layer in the multilayer structure may include the first heterocyclic compound.

The hole transport region may include a hole injection layer on the first electrode; a hole transport layer on the hole injection layer; and an electron blocking layer on the hole transport layer, and the electron blocking layer may include the first heterocyclic compound.

The emission layer may emit light by a luminescence mechanism based on the transition from a singlet state to a ground state.

The emission layer may emit thermally activated delayed fluorescence.

The first heterocyclic compound may be a compound of the following Compound Group 1:

[Compound Group 1]

1-1

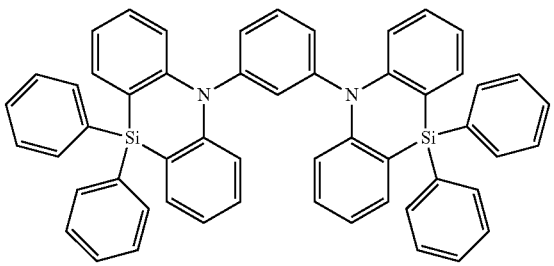

1-2

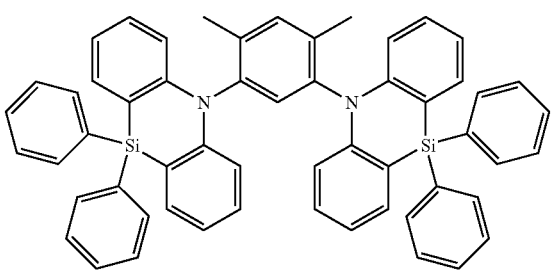

1-3

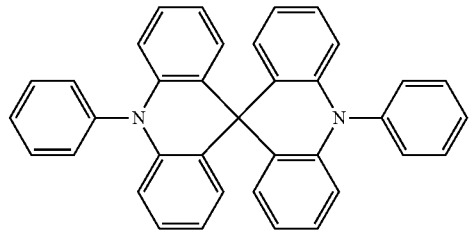

1-4

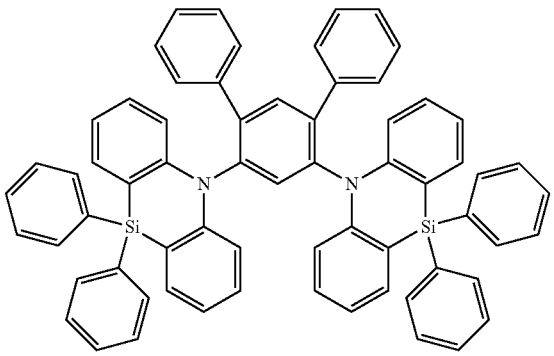

1-5
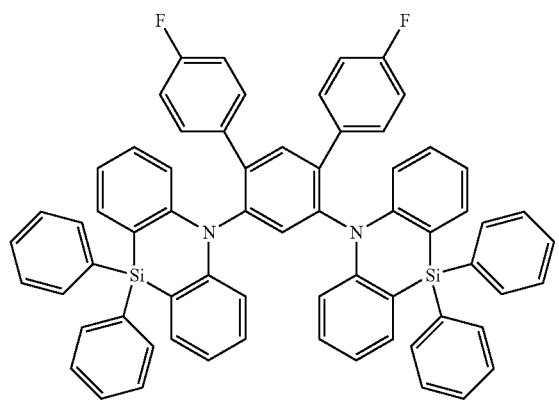
1-6
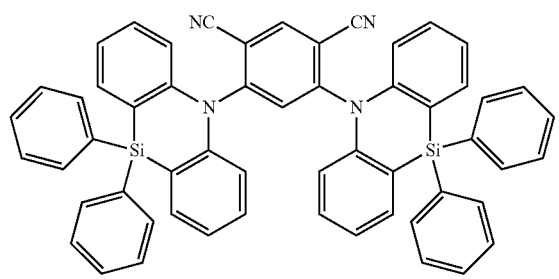
1-7
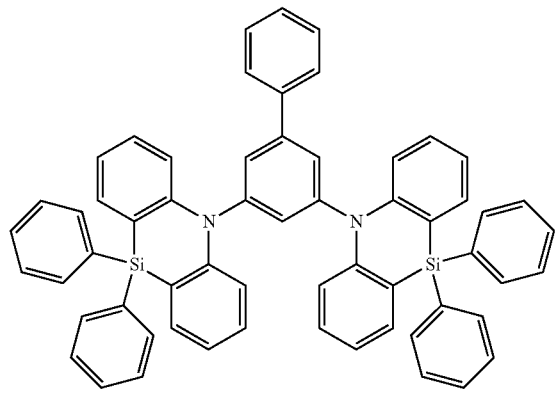
1-8
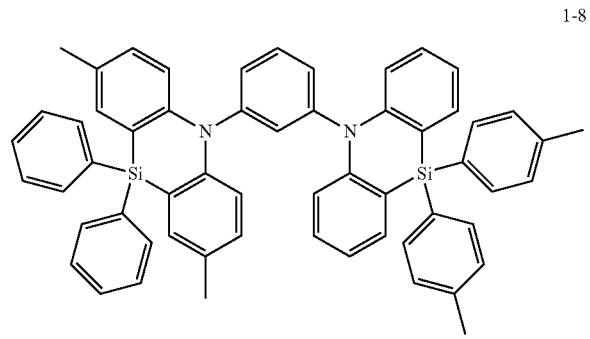
1-9
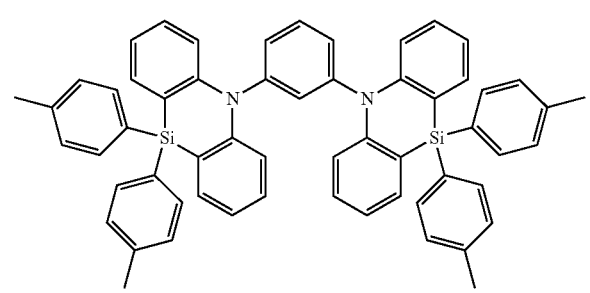
1-10
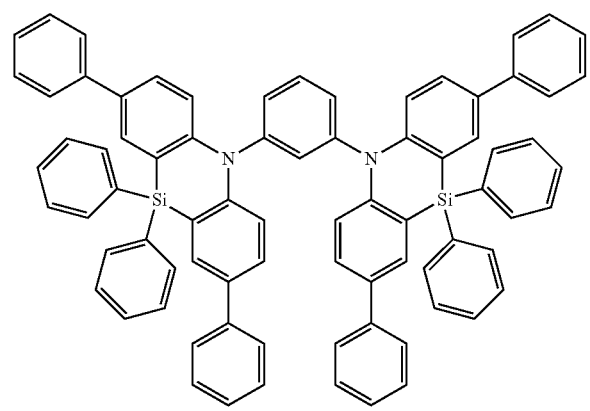
1-11
1-12
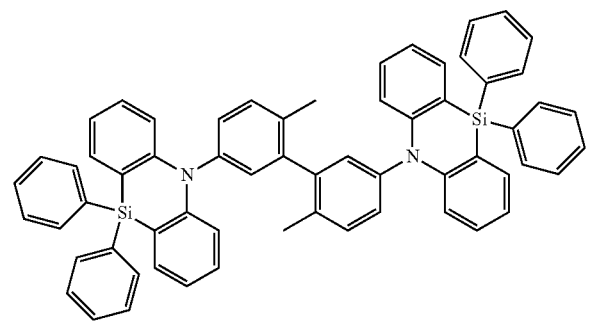

1-13
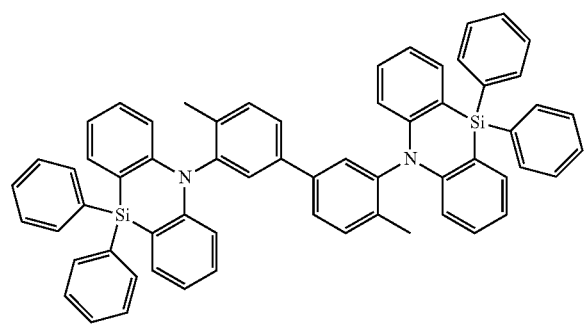
1-14
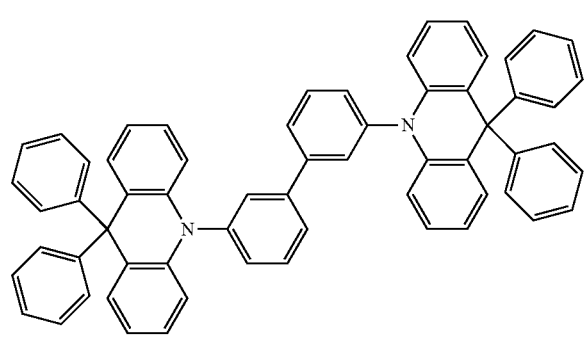
1-15
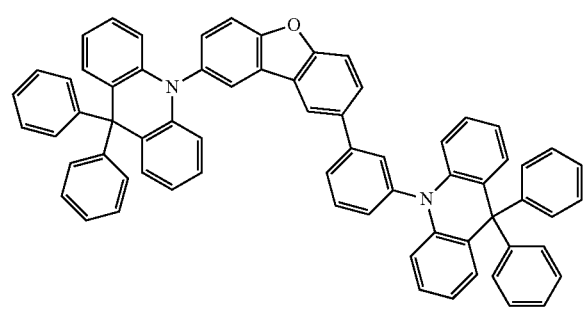
1-16
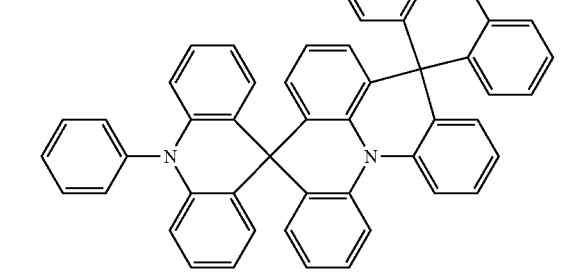
1-17
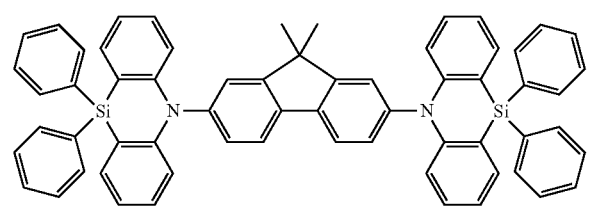
1-18
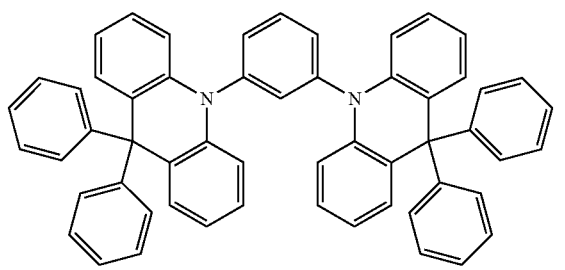
1-19
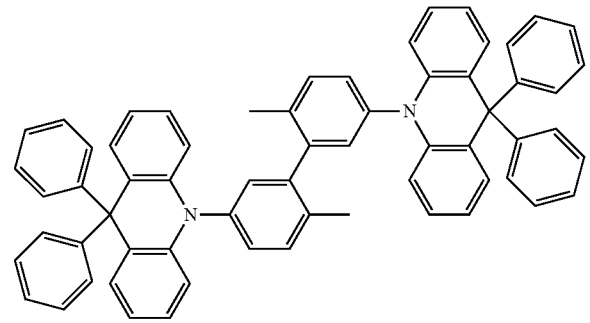
1-20
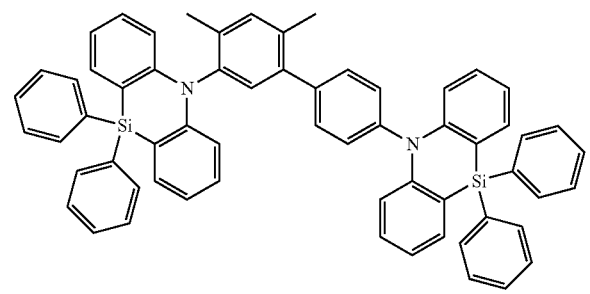
1-21
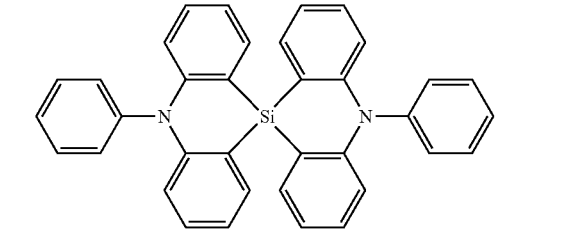

1-22
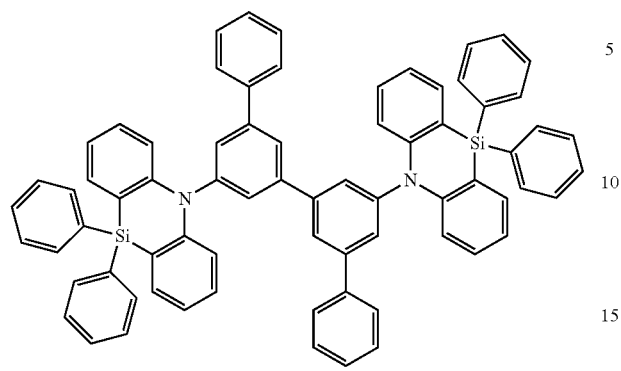
1-23
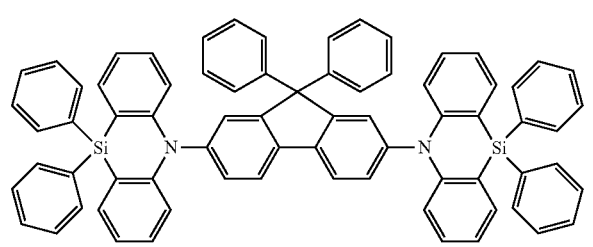
1-24
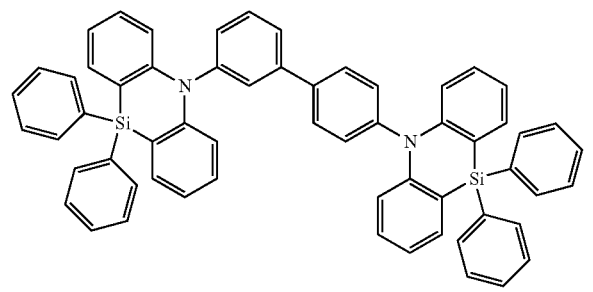
1-25
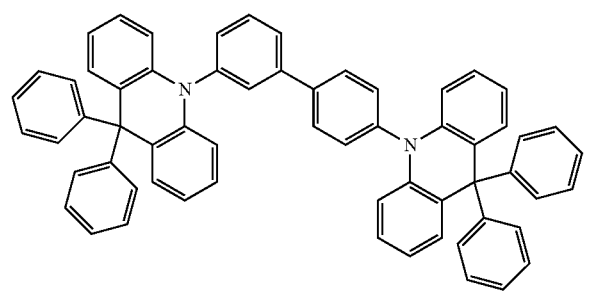
1-26
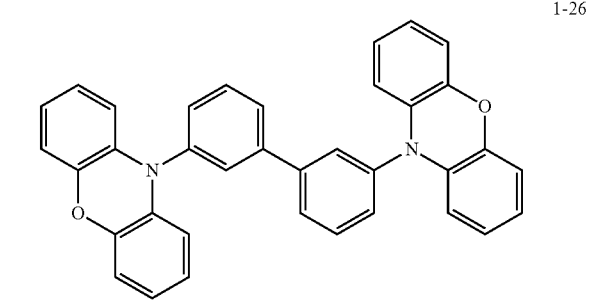
1-27
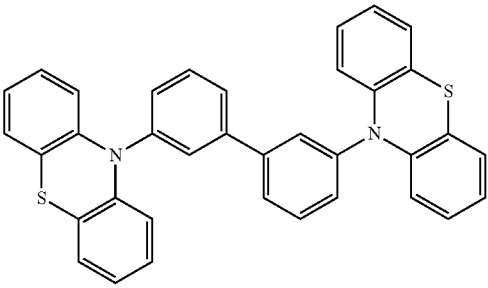
1-28
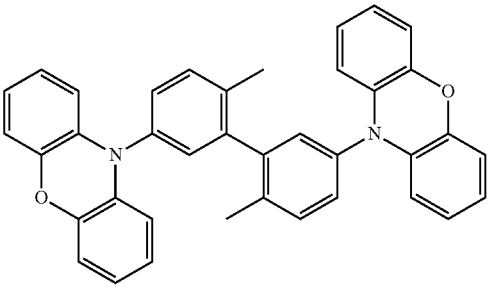
1-29
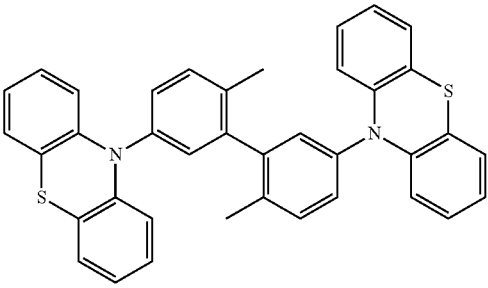
1-30
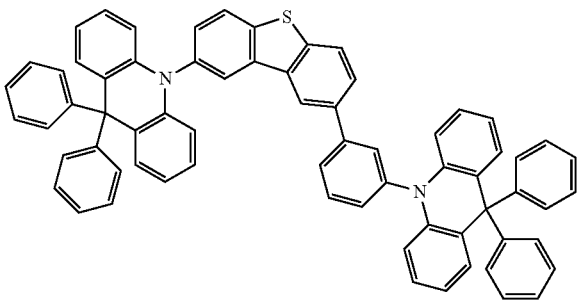
1-31
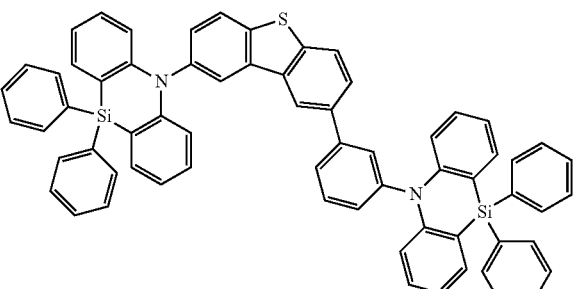

-continued
1-31
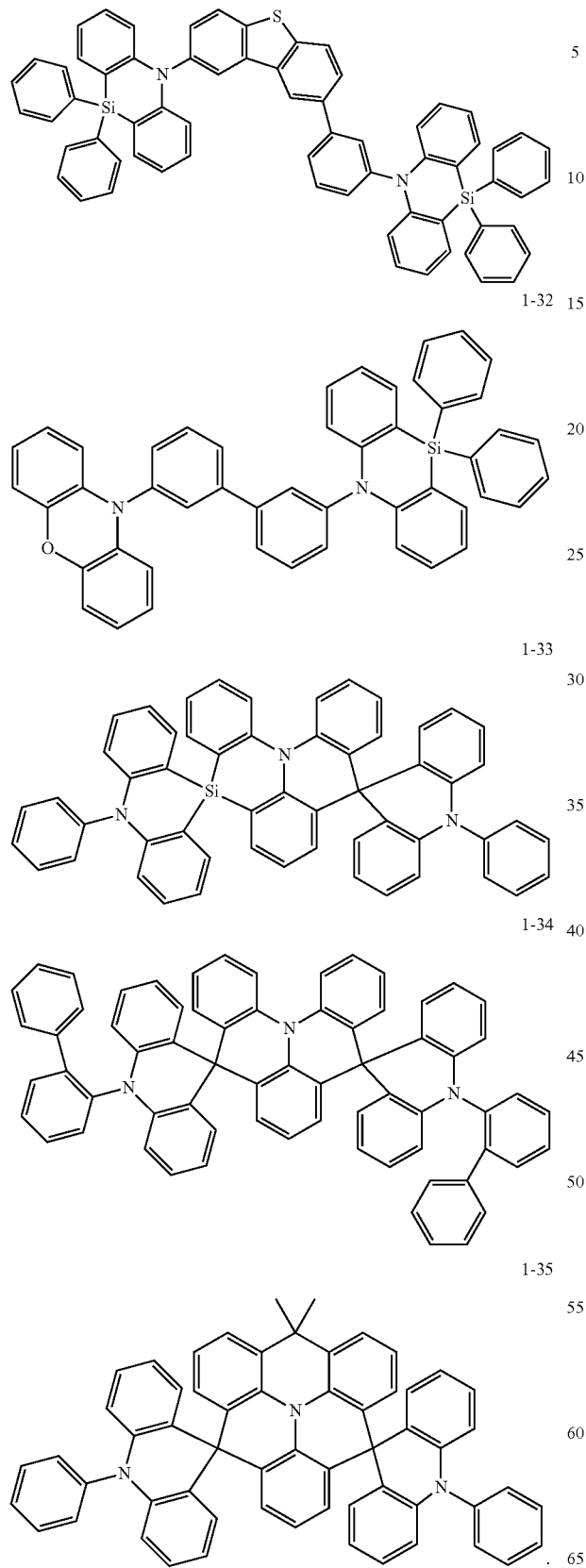
1-32
1-33
1-34
1-35
The second heterocyclic compound may be a compound of the following Compound Group 2:
[Compound Group 2]
2-1
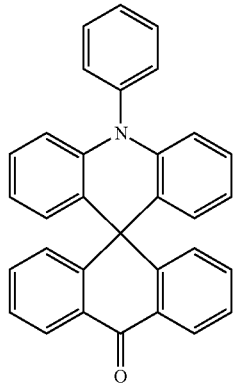
2-2
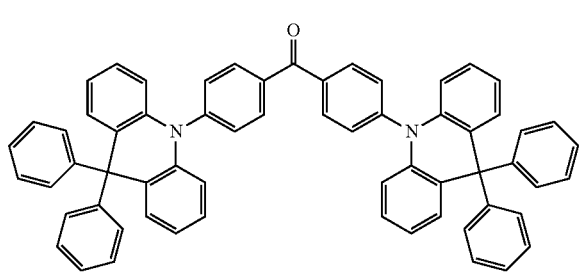
2-3
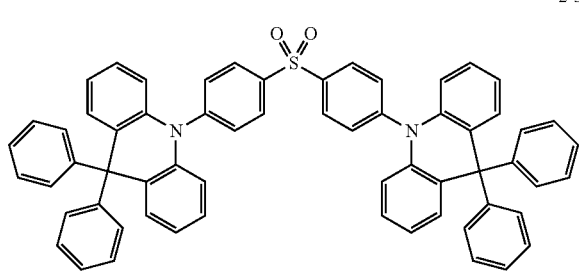
2-4
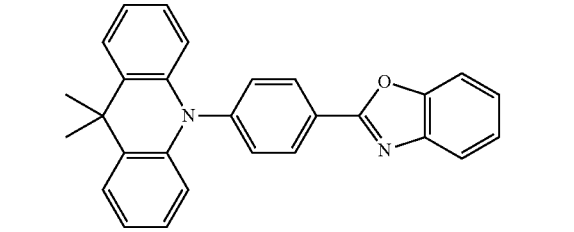
2-5
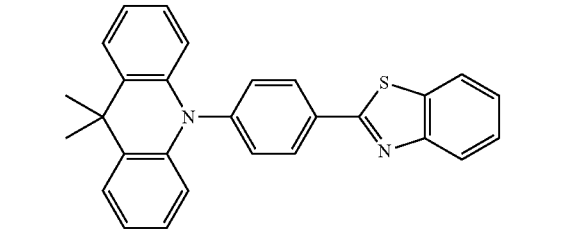

2-6
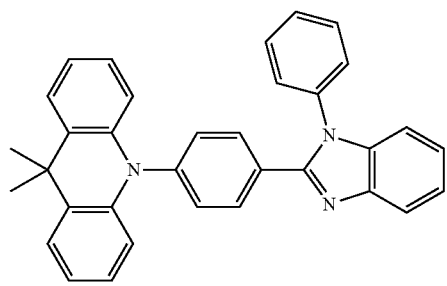
2-7
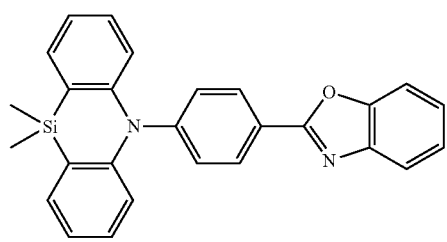
2-8
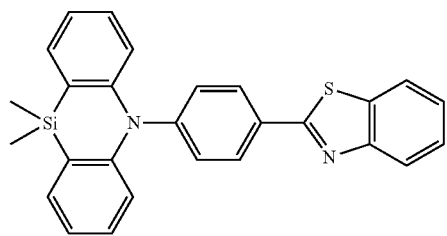
2-9
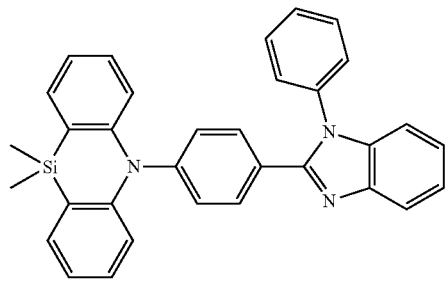
2-10
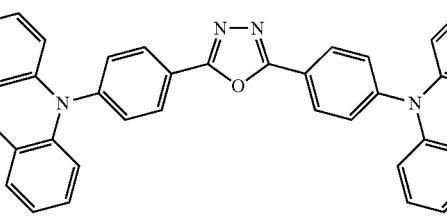
2-11
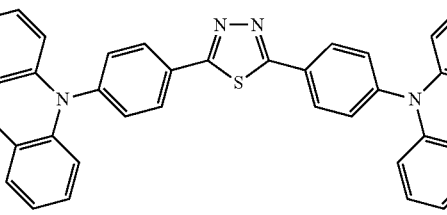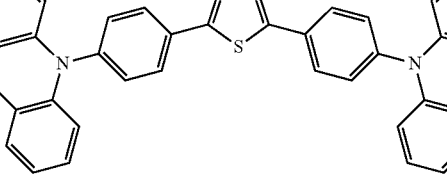
2-12
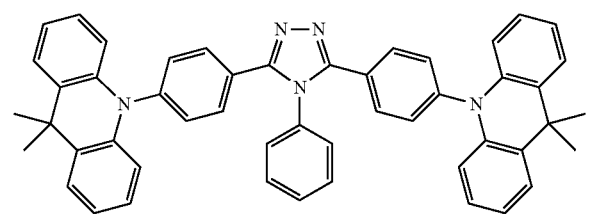
2-13
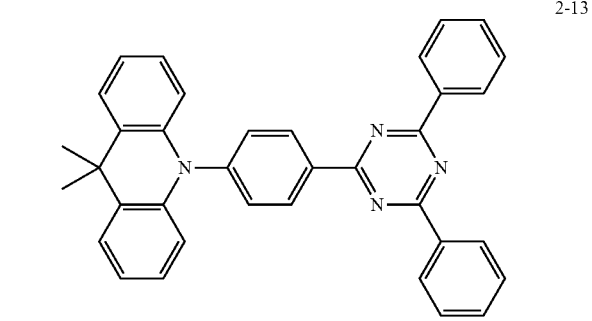
2-14
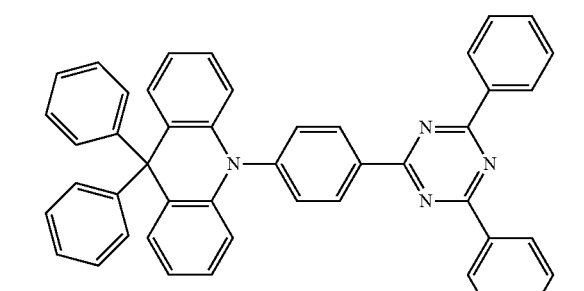
2-15
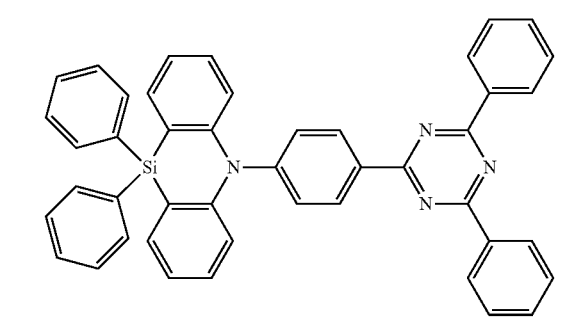
2-16
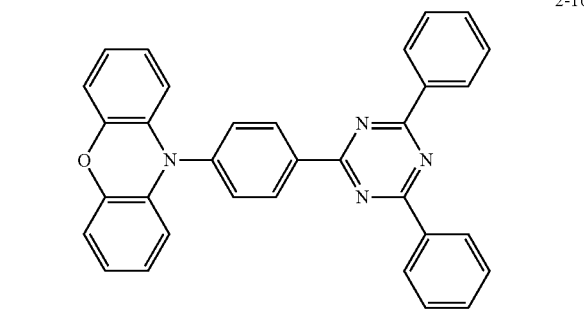

2-17 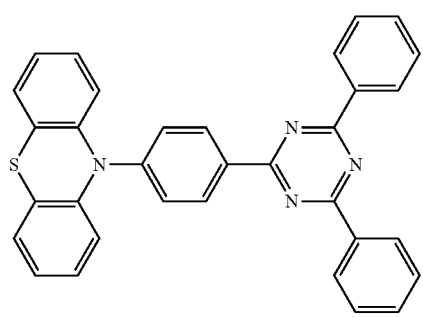
2-18 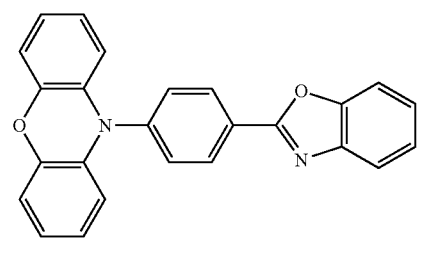
2-19 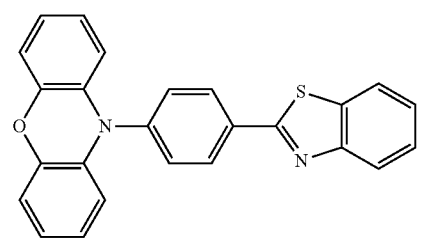
2-20 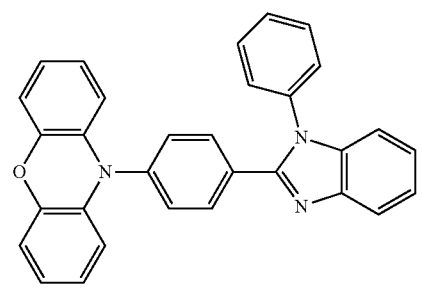
2-21 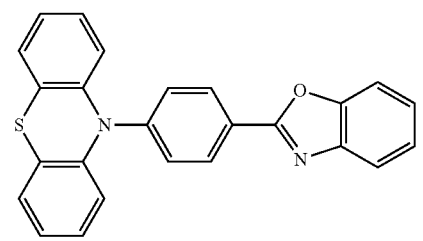
2-22 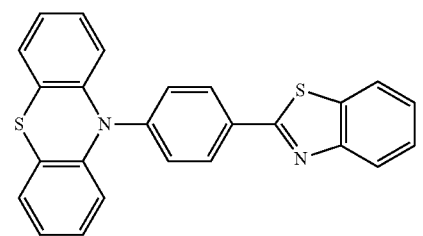
2-23 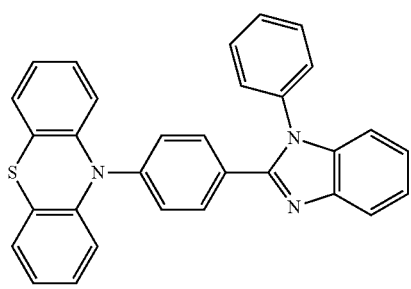
2-24 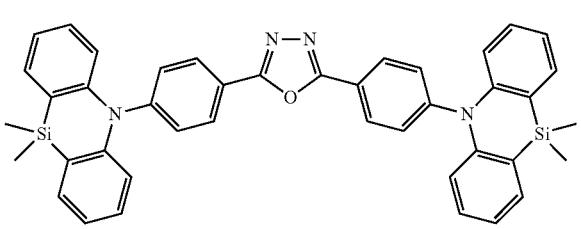
2-25 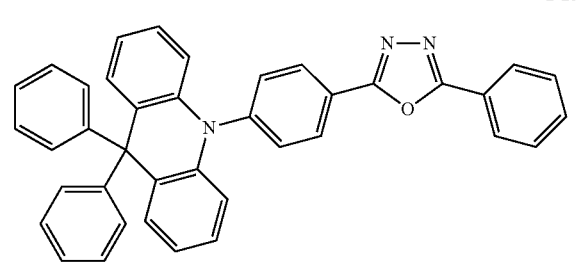
2-26 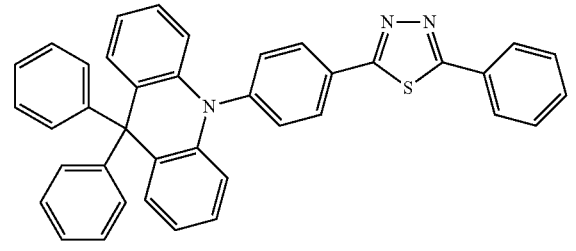
2-27 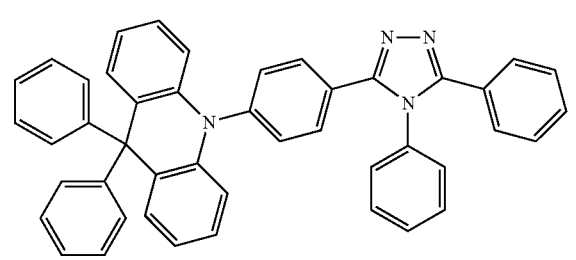
2-28 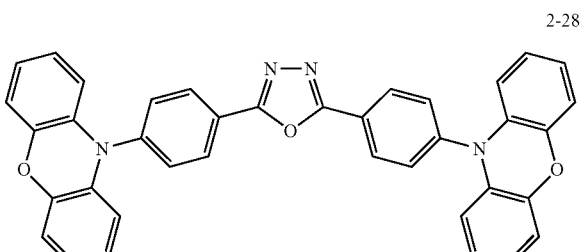

-continued

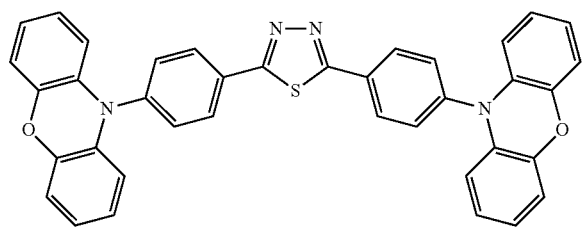
2-29

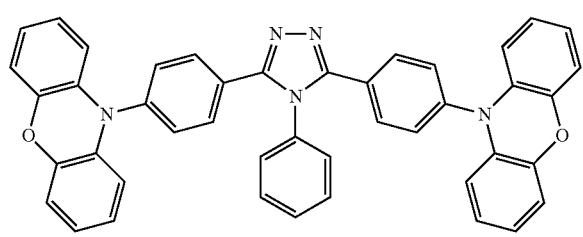
2-30

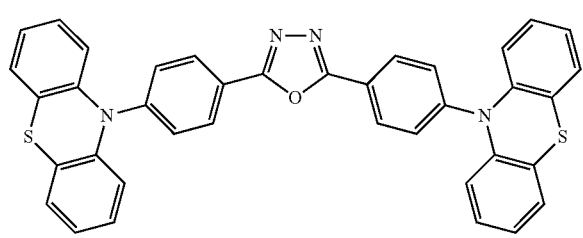
2-31

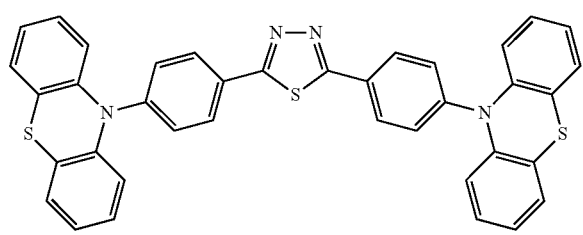
2-32

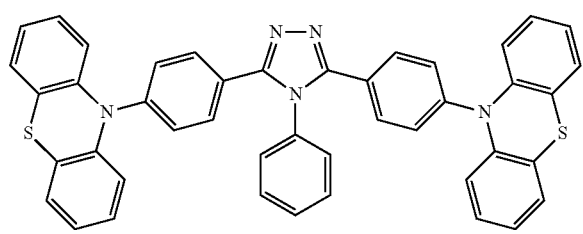
2-33

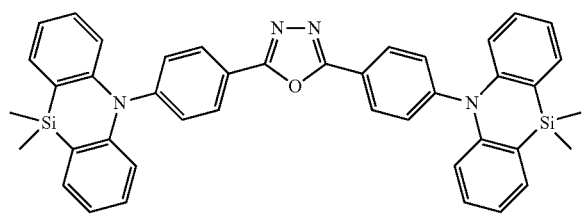
2-34

-continued

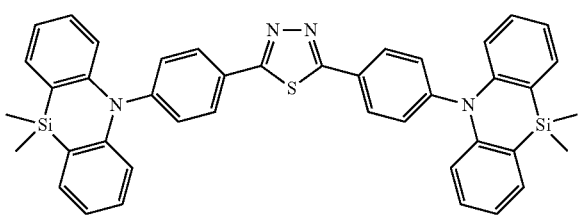
2-35

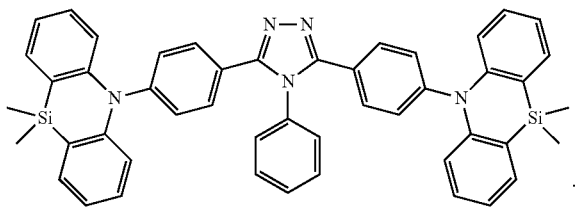
2-36

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
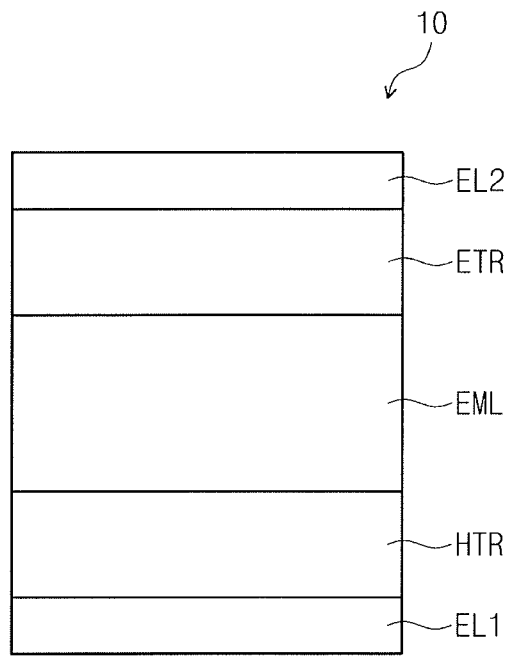
FIG. 1 illustrates a cross-sectional view of an organic electroluminescence device according to an embodiment of the present disclosure.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "includes," "including, "comprises," or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc.

is referred to as being 'on' another part, it can be directly on the other part, or intervening layers may also be present. On the contrary, when a layer, a film, a region, a plate, etc. is referred to as being 'under' another part, it can be directly under the other part, or intervening layers may also be present.

In the present disclosure, -* means a part to be connected, e.g., a bonding location.

In the present disclosure, "substituted or unsubstituted" may mean substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocycle, or unsubstituted. In addition, each of the substituent illustrated above may be substituted or unsubstituted. For example, a biphenyl group may be interpreted as an aryl group, or a phenyl group substituted with a phenyl group.

In the present disclosure, the description of a group forming a ring by combining with an adjacent group may mean forming substituted or unsubstituted cyclic hydrocarbon, or substituted or unsubstituted heterocycle by combining with an adjacent group. The cyclic hydrocarbon may include aliphatic cyclic hydrocarbon and aromatic cyclic hydrocarbon. The heterocycle may include aliphatic heterocycle and aromatic heterocycle. The cyclic hydrocarbon and heterocycle may be a monocycle or polycycle. In addition, the ring formed by combining with an adjacent group may be connected with another ring to form a spiro structure.

In the present disclosure, "adjacent group" may mean a substituent substituted at an atom which is directly connected to an atom at which a corresponding substituent is bonded, another substituent substituted at the atom at which a corresponding substituent is bonded, or the closest substituent to the corresponding substituent in consideration of a steric structure. For example, in 1,2-dimethylbenzene, two methyl groups may be interpreted as "adjacent groups" from each other, and in 1,1-diethylcyclopentene, two ethyl groups may be interpreted as "adjacent groups" from each other.

In the present disclosure, a halogen atom may include a fluorine atom, a chlorine atom, a bromine atom, or an iodine atom.

In the present disclosure, the alkyl may have a linear or branched chain or a cycle shape. The carbon number of the alkyl may be 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl means an optional functional group or substituent derived from aromatic cyclic hydrocarbon. The aryl may be monocyclic aryl or polycyclic aryl. The carbon number of the aryl for forming a ring may be 6 to 30, 6 to 20, or 6 to 15. Examples of the aryl may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the present disclosure, fluorenyl may be substituted, or two substituents may be combined with each other to form a Spiro structure. Examples of the substituted fluorenyl are as follows. However, an embodiment of the present disclosure is not limited thereto.

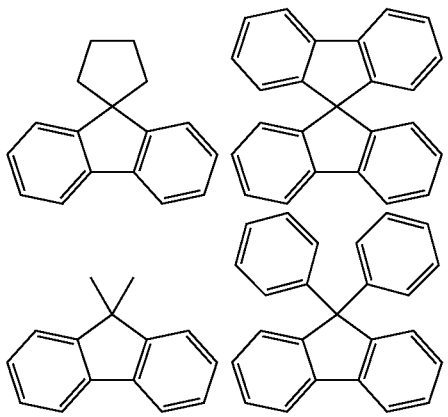

In the present disclosure, the heteroaryl may be heteroaryl including at least one of O, N, P, Si or S as a heteroatom. When the heteroaryl includes two heteroatoms, two heteroatoms may be the same or different from each other. The carbon number of the heteroaryl for forming a ring may be 2 to 30, or 2 to 20. The heteroaryl may be monocyclic heteroaryl or polycyclic heteroaryl. The heteroaryl may have a structure, for example of two rings or three rings. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophenyl, thienothiophene, benzofuranyl, phenanthroline, thiazolyl, isooxazolyl, oxadiazolyl, thiadiazolyl, benzothiazolyl, phenothiazinyl, dibenzosilole, dibenzofuranyl, etc., without limitation.

In the present disclosure, the explanation on the aryl may be applied to arylene except that the arylene is a divalent group.

In the present disclosure, the explanation on the heteroaryl may be applied to heteroarylene except that the heteroarylene is a divalent group.

In the present disclosure, the silyl may include alkylsilyl and arylsilyl. Examples of the silyl may include trimethylsilyl, triethylsilyl, t-butyldimethylsilyl, vinyldimethylsilyl, propyldimethylsilyl, triphenylsilyl, diphenylsilyl, phenylsilyl, etc., without limitation.

In the present disclosure, the boron group may include alkyl boron and aryl boron. Examples of the boron group may include trimethylboron, triethylboron, t-butyldimethylboron, triphenylboron, diphenylboron, phenylboron, etc., without limitation.

In the present disclosure, the alkenyl may be linear or branched. The carbon number is not specifically limited, but may be 2 to 30, 2 to 20, or 2 to 10. Examples of the alkenyl may include vinyl, 1-butenyl, 1-pentenyl, 1,3-butadienyl aryl, styrenyl, styrylvinyl, etc., without limitation.

In the present disclosure, the carbon number of the amino group is not specifically limited, but may be 1 to 30. The amino group may include an alkylamino group and arylamino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

Hereinafter, an organic electroluminescence device according to an embodiment will be explained.

Figure 2:
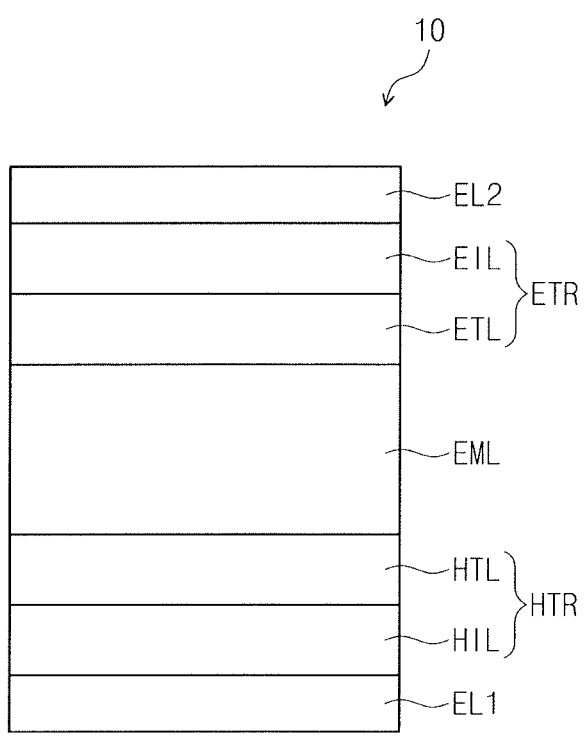
FIG. 2 illustrates a cross-sectional view of an organic electroluminescence device according to an embodiment of the present disclosure.
Figure 3:
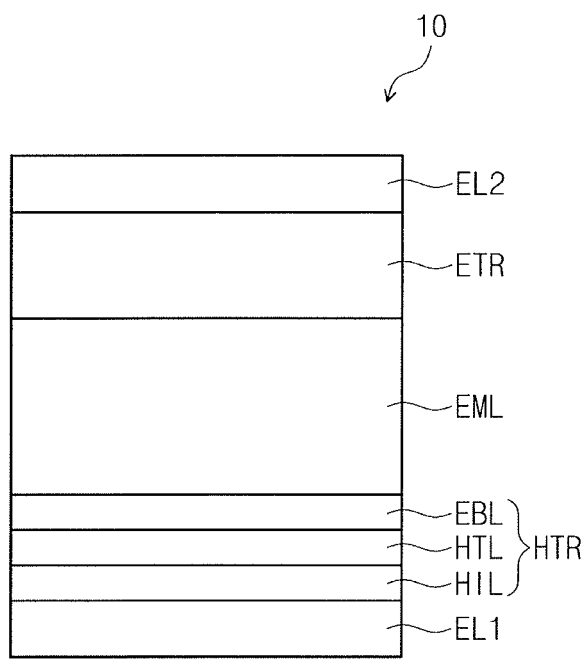
FIG. 3 illustrates a cross-sectional view of an organic electroluminescence device according to an embodiment of the present disclosure.

FIG. 1 illustrates a cross-sectional view of an organic electroluminescence device according to an embodiment of the present disclosure. FIG. 2 illustrates a cross-sectional view of an organic electroluminescence device according to an embodiment of the present disclosure. FIG. 3 illustrates a cross-sectional view of an organic electroluminescence device according to an embodiment of the present disclosure.

Referring to FIGS. 1 to 3, an organic electroluminescence device 10 according to an embodiment of the present disclosure may include a first electrode EL1, a hole transport region HTR, an emission layer EML, an electron transport region ETR, and a second electrode EL2.

In an implementation, the hole transport region HTR may include a first heterocyclic compound including 1 to 3 structures derived from a compound represented by Formula 1 below. In an implementation, the emission layer EML may include a second heterocyclic compound including 1 to 2 structures derived from a compound represented by Formula 1 below. For example, a structure derived from Formula 1 may refer to a structure including a moiety represented by Formula 1. For example, a compound including 2 structures derived from a compound represented by Formula 1 may refer to a compound including 2 moieties represented by Formula 1 which are bound together or share an atom of Formula 1.

[Formula 1]

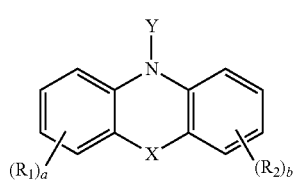

In Formula 1, X may be, e.g., O, S, $CR_wR_x$, or $SiR_yR_z$. Y, $R_w$ to $R_z$, $R_1$ and $R_2$ may each independently be or include, e.g., a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. In an implementation, Y, $R_w$ to $R_z$, $R_1$ and $R_2$ are separate or are combined with an adjacent group to form a ring. "a" and "b" may each independently be, e.g., an integer of 0 to 4.

In Formula 1, if "a" is 2 or more, a plurality of $R_1$ are the same or different. If "b" is 2 or more, a plurality of $R_2$ are the same or different.

The first electrode EL1 has conductivity. The first electrode EL1 may be a pixel electrode or an anode. The first electrode EL1 may be a transmissive electrode, a transflective electrode, or a reflective electrode. In the case where the first electrode EL1 is the transmissive electrode, the first electrode EL1 may be formed using a transparent metal oxide, e.g., indium tin oxide (ITO), indium zinc oxide (IZO), zinc oxide (ZnO), or indium tin zinc oxide (ITZO). In the case where the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, or a transparent layer formed using ITO, IZO, ZnO, or ITZO.

The hole transport region HTR may be provided on the first electrode EL1. The hole transport region HTR may include, e.g., at least one of a hole injection layer HIL, a hole transport layer HTL, a hole buffer layer, or an electron blocking layer EBL. The thickness of the hole transport region HTR may be, e.g., from about 1,000 Å to about 1,500 Å.

The hole transport region HTR may have a single layer formed using a single material, a single layer formed using a plurality of different materials, or a multilayer structure including a plurality of layers formed using a plurality of different materials.

In an implementation, if the hole transport region HTR has a multilayer structure, a layer contacting the emission layer EML in the multilayer structure may include the first heterocyclic compound. For example, referring to FIG. 2, if the hole transport region HTR includes a hole injection layer HIL disposed on the first electrode EL1, and a hole transport layer HTL disposed on the hole injection layer HIL, the hole transport layer HTL may include one or at least two of the first heterocyclic compounds. For example, referring to FIG. 3, if the hole transport region HTR includes a hole injection layer HIL disposed on the first electrode EL1, a hole transport layer HTL disposed on the hole injection layer HIL, and an electron blocking layer EBL disposed on the hole transport layer HTL, the electron blocking layer EBL may include one or at least two of the first heterocyclic compounds.

In an implementation, the hole transport region HTR may have the structure of a single layer such as a hole injection layer HIL and a hole transport layer HTL, or may have a single layer structure formed using a hole injection material and a hole transport material. In an implementation, the hole transport region HTR may have a structure of a single layer formed using a plurality of different materials, or a structure laminated one by one from the first electrode EL1 of hole injection layer HIL/hole transport layer HTL/hole buffer layer, hole injection layer HIL/hole buffer layer, or hole transport layer HTL/hole buffer layer. The hole buffer layer may compensate an optical resonance distance according to the wavelength of light emitted from the emission layer EML and increase light emission efficiency. Materials included in the hole transport region HTR may be used as materials included in the hole buffer layer.

The hole transport region HTR may be formed using various methods such as a vacuum deposition method, a spin coating method, a cast method, a Langmuir-Blodgett (LB)

method, an inkjet printing method, a laser printing method, and a laser induced thermal imaging (LITI) method.

The hole transport region HTR may include a first heterocyclic compound including 2 or 3 structures derived from the compound represented by Formula 1. In an implementation, the hole transport region HTR may include a first heterocyclic compound including 2 structures derived from a compound represented by Formula 1.

In an implementation, the hole transport region HTR may include a first heterocyclic compound represented by Formula 2 below.

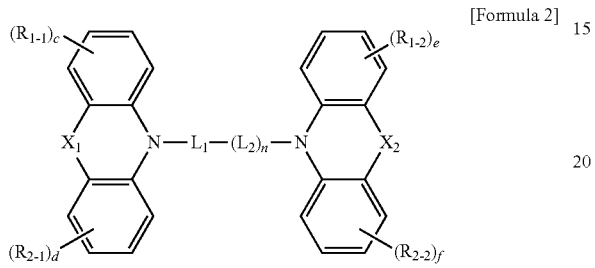

[Formula 2]

In Formula 2, $L_1$ and $L_2$ may each independently be or include, e.g., a substituted or unsubstituted arylene group having 6 to 30 ring carbon atoms, or a substituted or unsubstituted heteroarylene group having 2 to 30 ring carbon atoms, "n" may be 0 or 1, the definition of $R_{1-1}$, $R_{1-2}$, $R_{2-1}$ and $R_{2-2}$ may be the same as that of $R_1$ and $R_2$, "c" and "f" may each independently be an integer of 0 to 4, and the definition of $X_1$ and $X_2$ may be the same as that of X.

Formula 2 is an example of the first heterocyclic compound including 2 structures derived from the compound represented by Formula 1 (e.g., including 2 moieties represented by Formula 1).

In Formula 2, if "c" is 2 or more, a plurality of $R_{1-1}$ are the same or different, if "d" is 2 or more, a plurality of $R_{1-2}$ are the same or different, if "e" is 2 or more, a plurality of $R_{2-1}$ are the same or different, and if "f" is 2 or more, a plurality of $R_{2-2}$ are the same or different.

In an implementation, in Formula 2, $X_1$ and $X_2$ may be the same, $R_{1-1}$ and $R_{1-2}$ may be the same, $R_{2-1}$ and $R_{2-2}$ may be the same, "c" and "e" may be the same, and "d" and "f" may be the same. In an implementation, in Formula 2, $X_1$ and $X_2$ may be different from each other.

In an implementation, in Formula 2, $L_1$ may be or may include, e.g., a substituted or unsubstituted phenylene group, a substituted or unsubstituted divalent biphenyl group, or a substituted or unsubstituted fluorenylene group. In this case, "n" may be 0.

In an implementation, in Formula 2, $L_1$ may be or may include, e.g., a substituted or unsubstituted phenylene group. In an implementation, in Formula 2, $L_1$ may be, e.g., a group represented by one of the structures below.

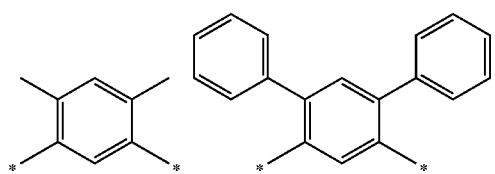

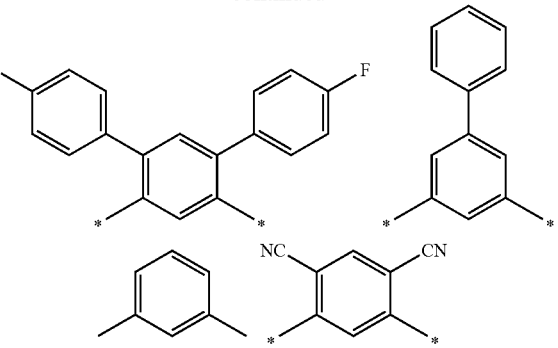

In an implementation, in Formula 2, $L_1$ may be, e.g., a substituted or unsubstituted fluorenylene group. In an implementation, in Formula 2, $L_1$ may be, e.g., a fluorenylene group unsubstituted or substituted with at least one of an alkyl group or an aryl group. In an implementation, in Formula 2, $L_1$ may be, e.g., a fluorenylene group disubstituted with alkyl groups, or a fluorenylene group disubstituted with aryl groups.

In an implementation, in Formula 2, $L_1$ may be, e.g., a substituted or unsubstituted divalent biphenyl group. In an implementation, in Formula 2, $L_1$ may be, e.g., a divalent biphenyl group unsubstituted or substituted with at least one of an alkyl group or an aryl group. In an implementation, in Formula 2, $L_1$ may be, e.g., a divalent biphenyl group disubstituted with alkyl groups, or a divalent biphenyl group disubstituted with aryl groups.

In an implementation, in Formula 2, "n" may be 1, $L_1$ may be, e.g., a substituted or unsubstituted arylene group having 6 to 30 ring carbon atoms, and $L_2$ may be, e.g., a substituted or unsubstituted heteroarylene group having 2 to 30 ring carbon atoms.

In an implementation, in Formula 2, "n" may be 1, $L_1$ may be, e.g., a substituted or unsubstituted phenylene group, and $L_2$ may be, e.g., a substituted or unsubstituted heteroarylene group. In an implementation, in Formula 2, "n" may be 1, $L_1$ may be, e.g., a substituted or unsubstituted phenylene group, and $L_2$ may be, e.g., a substituted or unsubstituted divalent carbazole group, a substituted or unsubstituted dibenzothiophene group, or a substituted or unsubstituted divalent dibenzofuran group.

In an implementation, in Formula 2, $X_1$ and $X_2$ may be each independently $CR_wR_x$ or $SiR_yR_z$. In an implementation, the compound represented by Formula 2 may be represented by, e.g., Formula 2-1 below.

[Formula 2-1]

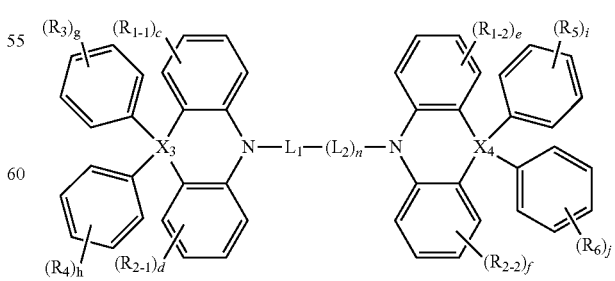

In Formula 2-1, $X_3$ and $X_4$ may each independently be, e.g., C or Si, $R_3$ to $R_6$ may each independently be or include, e.g., a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, "g" to "j" may each independently be, e.g., an integer of 0 to 5, and $L_1$, $L_2$, $R_{1-1}$, $R_{1-2}$, $R_{2-1}$, $R_{2-2}$, "c" to "f", and "n" may be the same as described above.

In an implementation, in Formula 2-1, each of "c" to "f" may be 0. In an implementation, in Formula 2-1, each of "c" and "d" may be 1, $R_{1-1}$ and $R_{2-1}$ may each independently be, e.g., a substituted or unsubstituted alkyl group having 1 to 20 carbon atoms. In an implementation, in Formula 2-1, each of "c" to "f" may be 1, and each of $R_{1-1}$, $R_{1-2}$, $R_{2-1}$, and $R_{2-2}$ may be, e.g., a substituted or unsubstituted aryl group having 6 to 30 ring carbon atoms.

In an implementation, in Formula 2-1, if "g" is 2 or more, a plurality of $R_3$ are the same or different, if "h" is 2 or more, a plurality of $R_4$ are the same or different, if "i" is 2 or more, a plurality of $R_5$ are the same or different, and if "j" is 2 or more, a plurality of $R_6$ are the same or different.

In an implementation, in Formula 2-1, each of "g" to "j" may be 0. In an implementation, each of "g" to "j" may be 1. Each of "g" to "j" may be 1, and each of $R_3$ to $R_6$ may be, e.g., a substituted or unsubstituted alkyl group having 1 to 20 carbon atoms. Each of "g" to "j" may be 1, and each of $R_3$ to $R_6$ may be, e.g., a substituted or unsubstituted methyl group, a substituted or unsubstituted ethyl group, a substituted or unsubstituted propyl group, or a substituted or unsubstituted butyl group.

In an implementation, in Formula 2-1, $X_3$ and $X_4$ may be the same.

In an implementation, the hole transport region HTR may include a first heterocyclic compound represented by Formula 3 below.

[Formula 3]

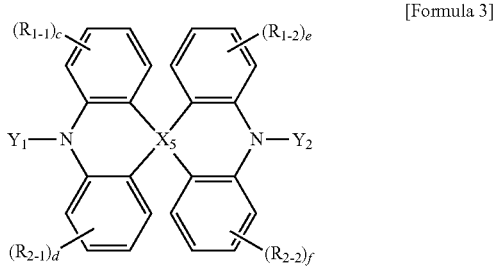

In Formula 3, $X_5$ may be, e.g., C or Si, the definition of $Y_1$ and $Y_2$ may be the same as that of Y, the definition of $R_{1-1}$, $R_{1-2}$, $R_{2-1}$ and $R_{2-2}$ may be the same as that of $R_1$ and $R_2$, and "c" to "f" may each independently be, e.g., an integer of 0 to 4.

In an implementation, in Formula 3, if "c" is 2 or more, a plurality of $R_{1-1}$ are the same or different, if "d" is 2 or more, a plurality of $R_{1-2}$ are the same or different, if "e" is 2 or more, a plurality of $R_{2-1}$ are the same or different, and if "f" is 2 or more, a plurality of $R_{2-2}$ are the same or different.

In an implementation, in Formula 3, each of "c" to "f" may be 0.

In an implementation, in Formula 3, $Y_1$ and $Y_2$ may each independently be, e.g., a substituted or unsubstituted aryl group having 6 to 30 ring carbon atoms.

In an implementation, in Formula 3, $Y_1$ and $Y_2$ may be the same. In an implementation, in Formula 3, $Y_1$ and $Y_2$ may be the same, $R_{1-1}$ and $R_{1-2}$ may be the same, $R_{2-1}$ and $R_{2-2}$ may be the same, "c" and "e" may be the same, and "d" and "f" may be the same.

In an implementation, the compound represented by Formula 3 may be represented by, e.g., Formula 3-1 below.

[Formula 3-1]

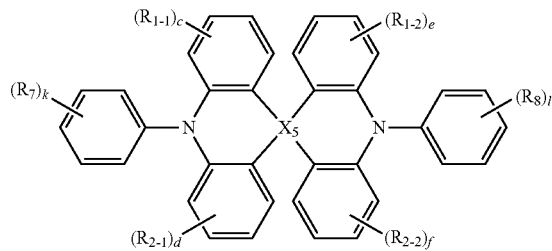

In Formula 3-1, $R_7$ and $R_8$ may each independently be, e.g., a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, "k" and "l" may each independently be, e.g., an integer of 0 to 5, $X_5$, $R_{1-1}$, $R_{1-2}$, $R_{2-1}$, $R_{2-2}$, and "c" to "f" may be the same as described above.

Formula 3-1 is an example of the first heterocyclic compound including 2 structures derived from a compound represented by Formula 1.

In an implementation, in Formula 3-1, if "k" is 2 or more, a plurality of $R_7$ are the same or different, and if "l" is 2 or more, a plurality of $R_8$ are the same or different.

In an implementation, in Formula 3-1, each of "k" and "l" may be 0.

In an implementation, the hole transport region HTR may include a first heterocyclic compound represented by Formula 3-2 below.

[Formula 3-2]

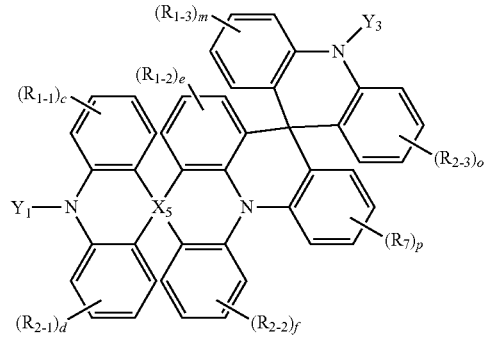

In Formula 3-2, $Y_3$ may be, e.g., a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_{1-3}$, $R_{2-3}$ and $R_7$ may each independently be, e.g., a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. In an implementation, $R_{1-3}$, $R_{2-3}$ and $R_7$ may be separate or may be combined with an adjacent group to form a ring. "e" may be, e.g., an integer of 0 to 3, "m", "o" and "p" may each independently be, e.g., an integer of 0 to 4, and $X_5$, $Y_1$, $R_{1-1}$, $R_{1-2}$, $R_{2-1}$, $R_{2-2}$, and "c", "d" and "f" may be the same as described above.

Formula 3-2 is an example of the first heterocyclic compound including 3 structures derived from the compound represented by Formula 1.

In an implementation, in Formula 3-2, if "m" is 2 or more, a plurality of $R_{1-3}$ are the same or different, and, if "o" is 2 or more, a plurality of $R_{2-3}$ are the same or different.

In an implementation, in Formula 3-2, $Y_1$ and $Y_3$ may each independently be, e.g., a substituted or unsubstituted aryl group having 6 to 30 ring carbon atoms. In an implementation, in Formula 3-2, at least one of $Y_1$ and $Y_3$ may be, e.g., a substituted or unsubstituted phenyl group.

In an implementation, in Formula 3-2, $X_5$ may be C.

In an implementation, the hole transport region HTR may include, e.g., a first heterocyclic compound of the following Compound Group 1:

[Compound Group 1]

1-1

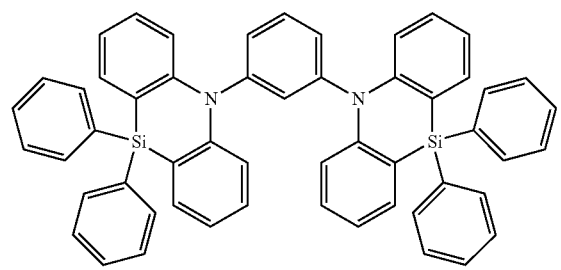

1-2

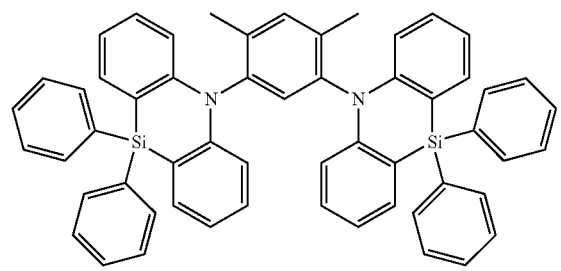

1-3

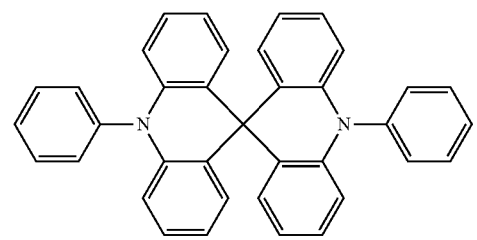

-continued 1-4

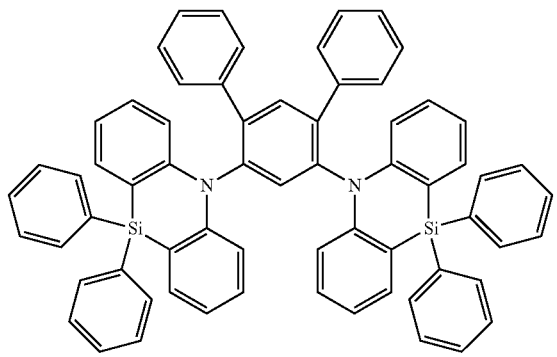

1-5

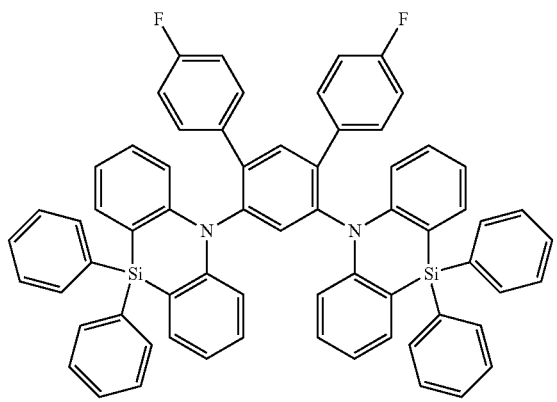

1-6

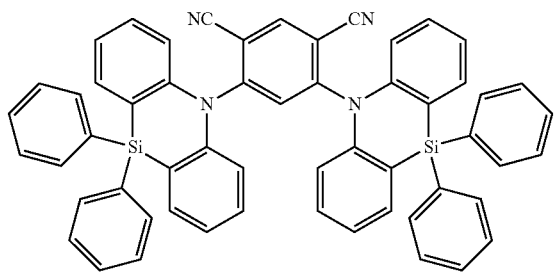

1-7

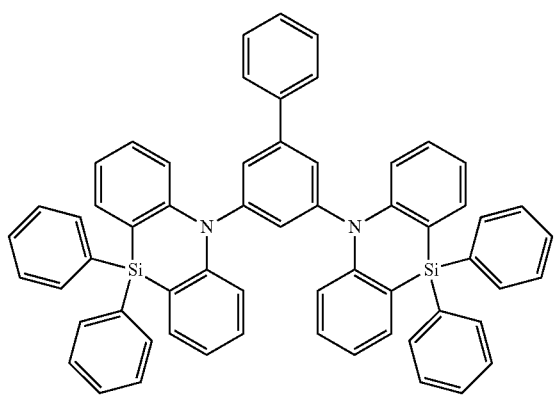

1-8
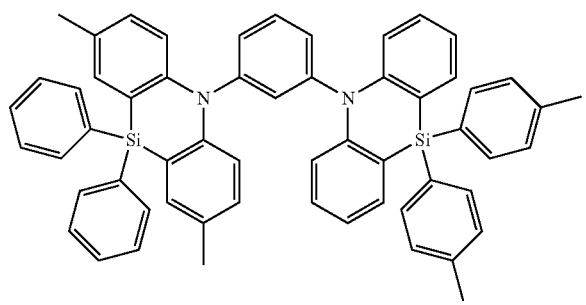
1-12
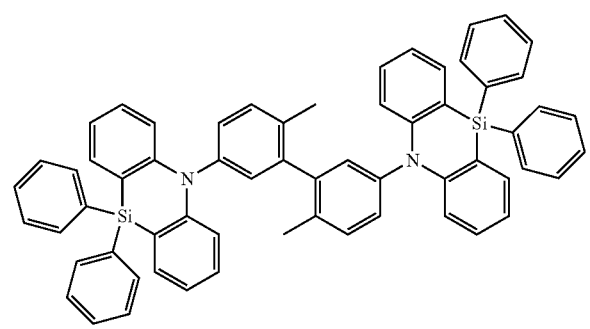
1-9
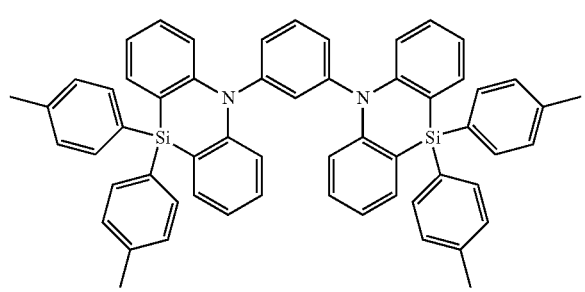
1-13
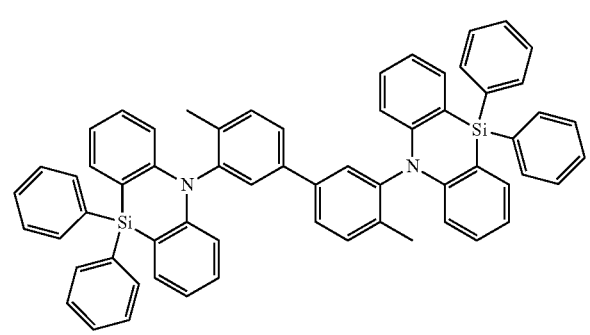
1-10
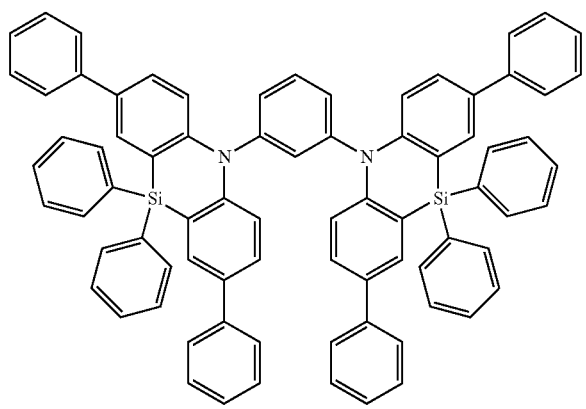
1-14
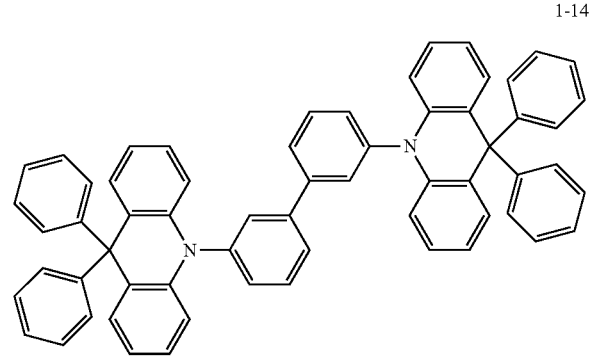
1-11
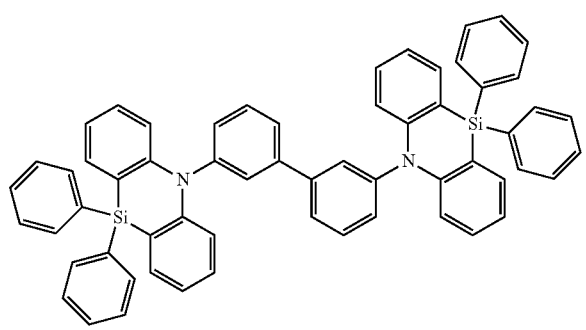
1-15
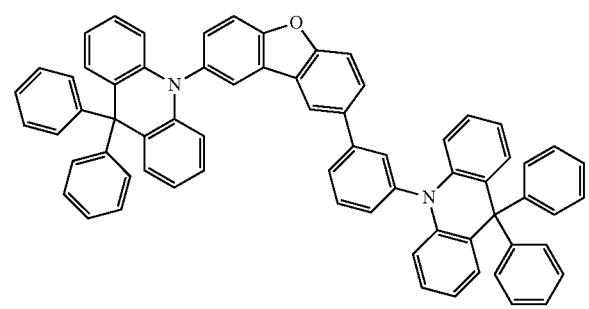

1-16
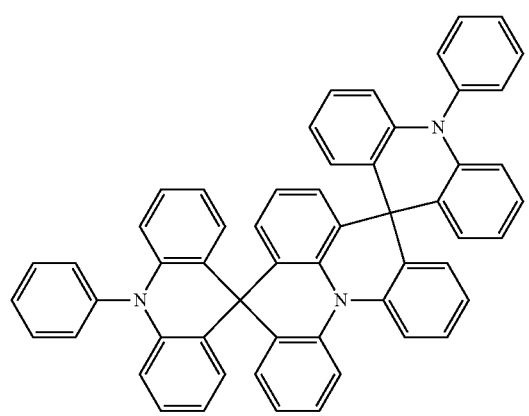
1-17
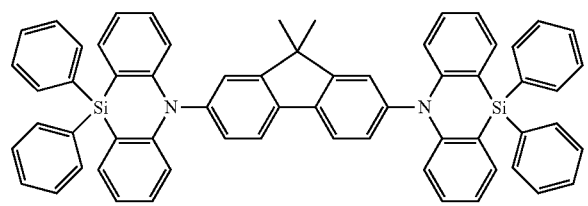
1-18
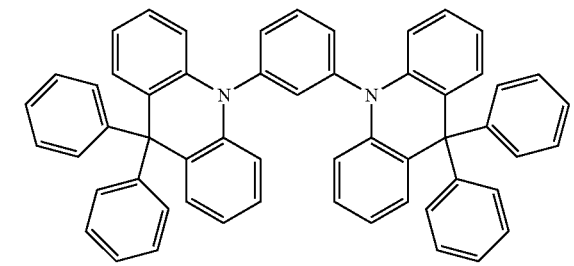
1-19
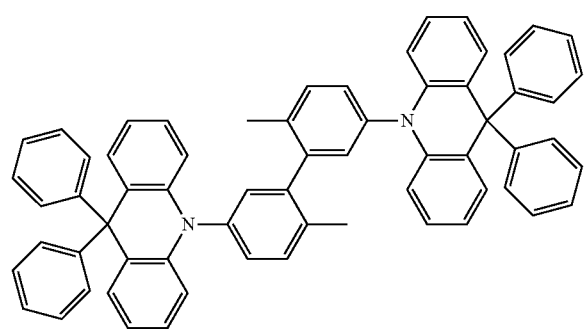
1-20
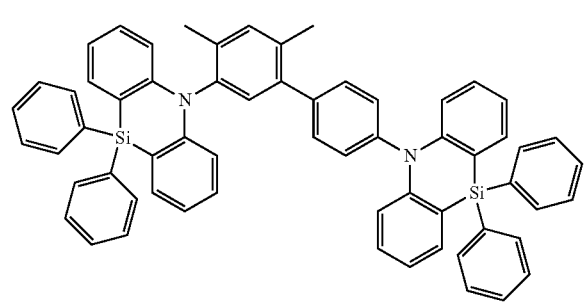
1-21
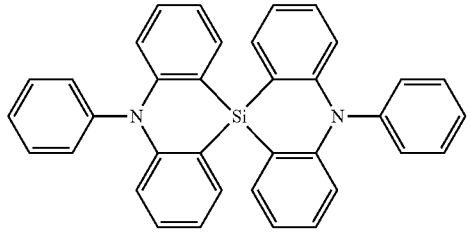
1-22
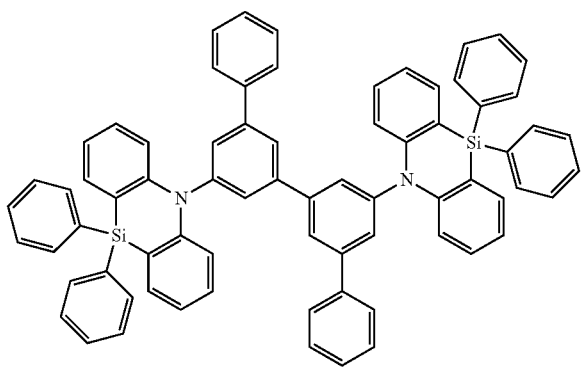
1-23
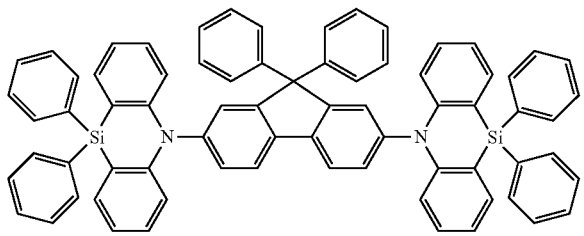
1-24
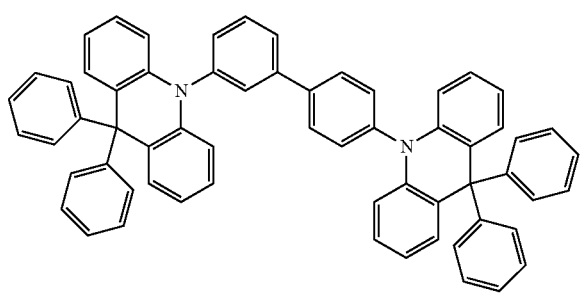
1-25

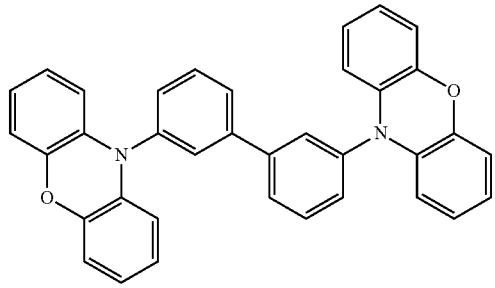

-continued 1-35

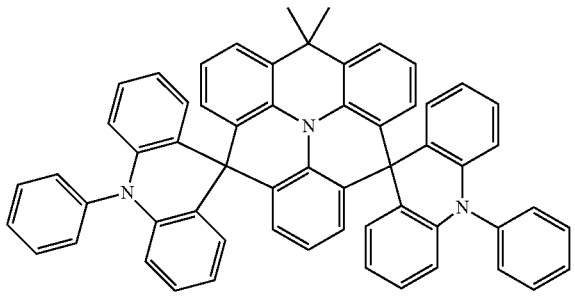

The hole injection layer HIL may include, e.g., a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

In an implementation, if the hole transport layer HTL does not include the first heterocyclic compound, the hole transport layer may include a suitable hole transport material. The hole transport layer HTL may include, e.g., carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc. In an implementation, even if the hole transport layer HTL includes the first heterocyclic compound, it may further include the suitable hole transport material.

The thickness of the hole transport region HTR may be from about 100 Å to about 10,000 Å, e.g., from about 100 Å to about 1,000 Å. If the hole transport region HTR includes all the hole injection layer HIL, the hole transport layer HTL, and the electron blocking layer EBL, the thickness of the hole injection layer HIL may be, e.g., from about 100 Å to about 1,000 Å, the thickness of the hole transport layer HTL may be from about 30 Å to about 1,000 Å, and the thickness of the electron blocking layer EBL may be from about 30 Å to about 100 Å. If the thicknesses of the hole transport region HTR, the hole injection layer HIL, the hole transport layer HTL, and the electron blocking layer EBL satisfy the above-described ranges, satisfactory hole transport properties may be obtained without the substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, e.g., a p-dopant. The p-dopant may be, e.g., one of quinone derivatives, metal oxides, or cyano group-containing compounds. Examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide, and molybdenum oxide.

The emission layer EML may be provided on the hole transport region HTR. The emission layer EML is a layer emitting light by fluorescence or phosphorescence, and is formed to a thickness of, e.g., from about 100 Å to about 600 Å.

In an implementation, the emission layer EML may have a single layer formed using a single material, a single layer formed using a plurality of different materials, or a multi-layer structure having a plurality of layers formed using a plurality of different materials.

As described above, the emission layer EML may include the second heterocyclic compound including 1 or 2 structures derived from a compound represented by Formula 1.

The emission layer EML may include a host and a dopant.

In an implementation, the second heterocyclic compound may be the same as the first heterocyclic compound. In an implementation, the second heterocyclic compound may be the host of an emission layer. In an implementation, the second heterocyclic compound may be different from the first heterocyclic compound. In an implementation, the second heterocyclic compound may be the dopant of an emission layer.

In an implementation, the hole transport region HTR may include the first heterocyclic compound including 2 structures derived from the compound represented by Formula 1, and the emission layer EML may include the second heterocyclic compound including 1 structure derived from the compound represented by Formula 1.

In an implementation, the emission layer EML may include the second heterocyclic compound including 1 or 2 structures derived from the compound represented by Formula 1, and a compound having higher triplet energy (T1) than the second heterocyclic compound. For example, the second heterocyclic compound may be the dopant of the emission layer EML.

In an implementation, the emission layer EML may include a second heterocyclic compound represented by the following Formula 4.

[Formula 4]

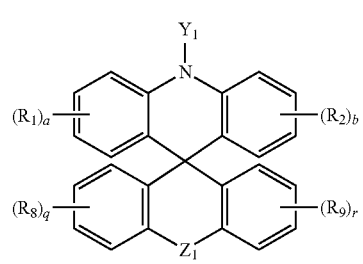

In Formula 4, $Z_1$ may be, e.g., —CO—, or —SO$_2$—. $R_8$ and $R_9$ may each independently be or include, e.g., a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. "q" and "r" may each independently be, e.g., an integer of 0 to 4. The definition of $Y_1$ may be the same as that of Y, and $R_1$, R2, "a" and "b" may be the same as described above.

Formula 4 is an example of the second heterocyclic compound including 1 structure derived from the compound represented by Formula 1.

In an implementation, in Formula 4, if "q" is 2 or more, a plurality of $R_8$ are the same or different, and if "r" is 2 or more, a plurality of $R_9$ are the same or different.

In an implementation, in Formula 4, $Z_1$ may be —CO— (carbonyl group).

In an implementation, in Formula 4, $Y_1$ may be, e.g., a substituted or unsubstituted aryl group having 6 to 30 ring carbon atoms. In an implementation, in Formula 4, $Y_1$ may be, e.g., a substituted or unsubstituted aryl group having 6 to 15 ring carbon atoms. In an implementation, in Formula 4, $Y_1$ may be, e.g., a substituted or unsubstituted phenyl group.

In an implementation, in Formula 4, each of "a", "b", "q" and "r" may be 0.

In an implementation, the emission layer EML may include a second heterocyclic compound represented by the following Formula 5.

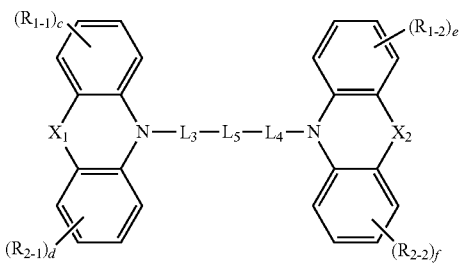

[Formula 5]

In Formula 5, $L_3$ and $L_4$ may each independently be or include, e.g., a substituted or unsubstituted arylene group having 6 to 30 ring carbon atoms or a substituted or unsubstituted heteroarylene group having 2 to 30 ring carbon atoms. $L_5$ may be, e.g., —CO—, or —SO$_2$—. The definition of $R_{1-1}$, $R_{1-2}$, $R_{2-1}$, and $R_{2-2}$ may be the same as that of $R_1$ and $R_2$. "c" to "F" may each independently be, e.g., an integer of 0 to 4, and the definition of $X_1$ and $X_2$ may be the same as that of X.

Formula 5 is an example of the second heterocyclic compound including 2 structures derived from a compound represented by Formula 1.

In an implementation, in Formula 5, if "c" is 2 or more, a plurality of $R_{1-1}$ are the same or different, if "d" is 2 or more, a plurality of $R_{1-2}$ are the same or different, if "e" is 2 or more, a plurality of $R_{2-1}$ are the same or different, and if "f" is 2 or more, a plurality of $R_{2-2}$ are the same or different.

In an implementation, in Formula 5, each of "c" to "1" may be 0.

In an implementation, in Formula 5, $L_3$ and $L_4$ may each independently be, e.g., a substituted or unsubstituted arylene group having 6 to 30 ring carbon atoms. In an implementation, in Formula 5, $L_3$ and $L_4$ may each independently be, e.g., a substituted or unsubstituted arylene group having 6 to 15 ring carbon atoms. In an implementation, in Formula 5, $L_3$ and $L_4$ may each independently be, e.g., a substituted or unsubstituted phenylene group.

In an implementation, in Formula 5, $L_3$ and $L_4$ may be the same.

In an implementation, in Formula 5, $X_1$ and $X_2$ may be the same. In an implementation, in Formula 5, each of $X_1$ and $X_2$ may be, e.g., $CR_wR_x$, where of $R_w$ and $R_x$ may each independently be, e.g., a substituted or unsubstituted aryl group having 6 to 30 ring carbon atoms. In an implementation, in Formula 5, each $X_1$ and $X_2$ may be, e.g., $CR_wR_x$, where of $R_w$ and $R_x$ may each independently be, e.g., a substituted or unsubstituted phenyl group.

In an implementation, in Formula 5, $L_3$ and $L_4$ may be the same, $X_1$ and $X_2$ may be the same, $R_{1-1}$ and $R_{1-2}$ may be the same, $R_{2-1}$ and $R_{2-2}$ may be the same, "c" and "e" may be the same, and "d" and "1" may be the same.

In an implementation, the emission layer EML may include a second heterocyclic compound represented by the following Formula 6.

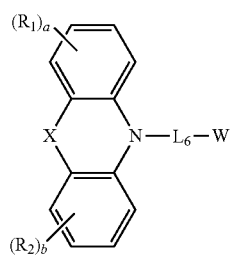

[Formula 6]

In Formula 6, X, $R_1$, $R_2$, "a" and "b" may be the same as defined In Formula 1. In an implementation, $L_6$ may be, e.g., a substituted or unsubstituted arylene group having 6 to 30 ring carbon atoms, and W may be, e.g., a substituted or unsubstituted triazine group or a group represented by the following Formula 7.

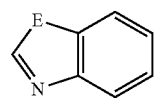

[Formula 7]

In Formula 7, E may be, e.g., O, S, or NR', in which R' may be, e.g., a hydrogen atom, a deuterium atom, a substituted or unsubstituted alkyl group having 1 to 10 carbon atoms, or a substituted or unsubstituted aryl group having 6 to 30 ring carbon atoms.

In an implementation, in Formula 6, $L_6$ may be, e.g., a substituted or unsubstituted phenylene group. In an implementation, in Formula 6, $L_6$ may be, e.g., a substituted or unsubstituted 1,4-pheylene group.

In an implementation, in Formula 6, W may be, e.g., a triazine group unsubstituted or substituted with at least one aryl group. In an implementation, in Formula 6, W may be, e.g., an aryl group unsubstituted or substituted with at least one phenyl group.

In an implementation, in Formula 7, if E is NR', R' may be, e.g., a substituted or unsubstituted phenyl group.

In an implementation, the emission layer EML may include at least one second heterocyclic compound of Compound Group 2 below.

[Compound Group 2]
2-1
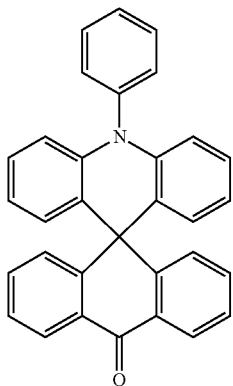
2-2
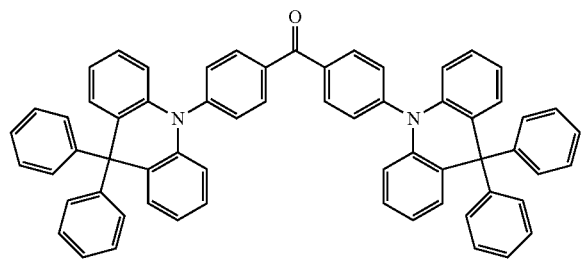
2-3
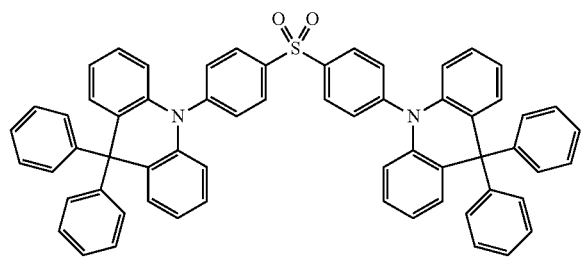
2-4
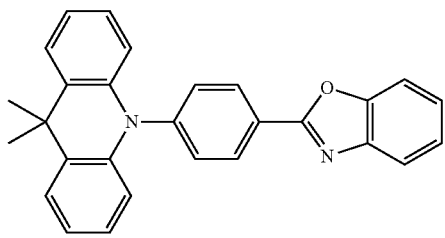
2-5
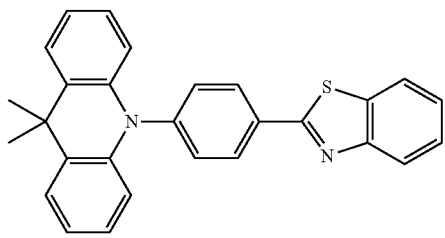
2-6
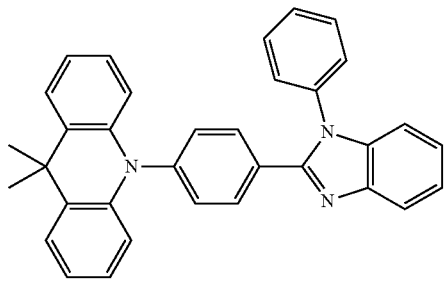
2-7
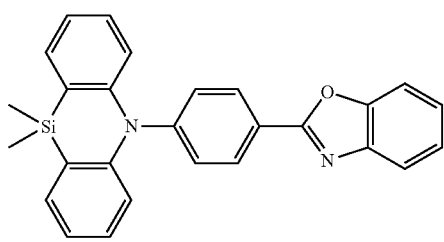
2-8
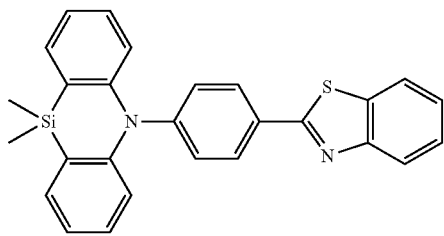
2-9
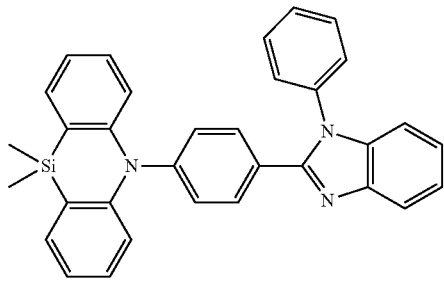
2-10
2-11

2-12
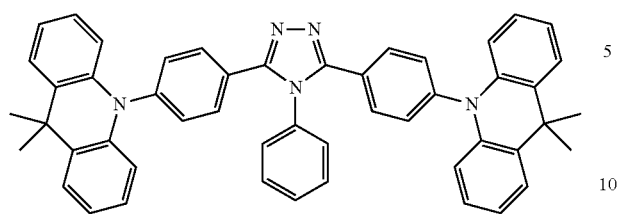
2-13
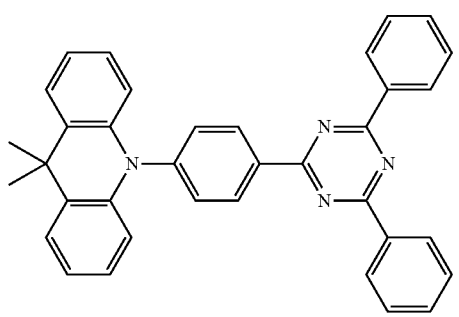
2-14
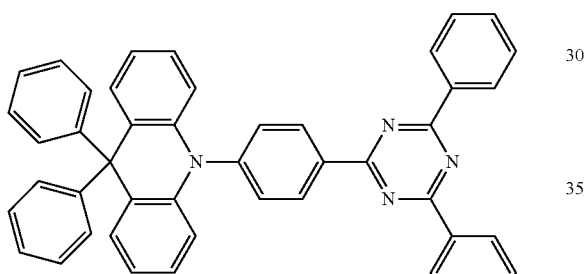
2-15
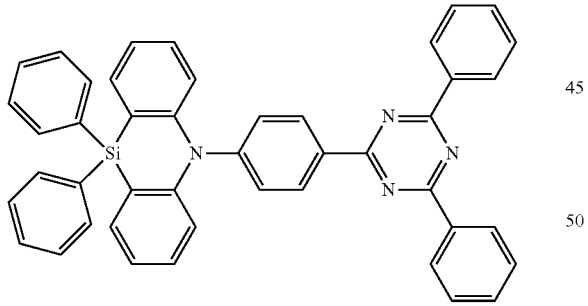
2-16
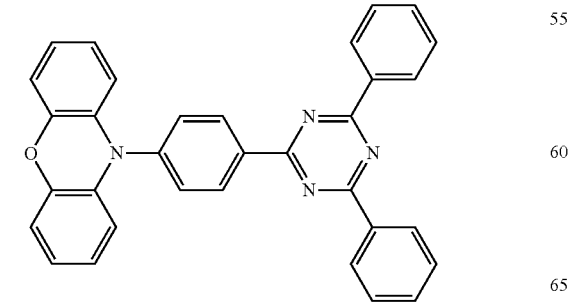
2-17
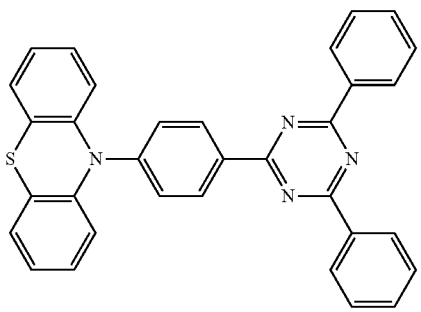
2-18
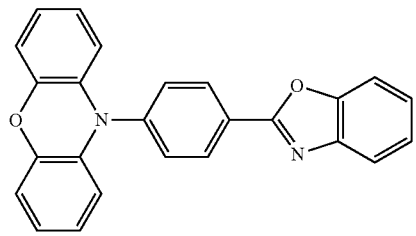
2-19
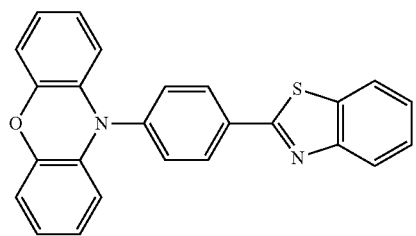
2-20
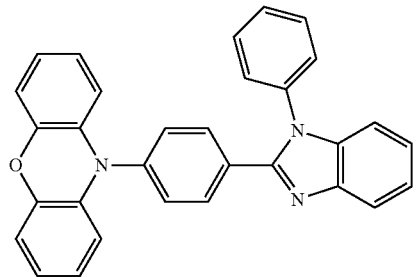
2-21
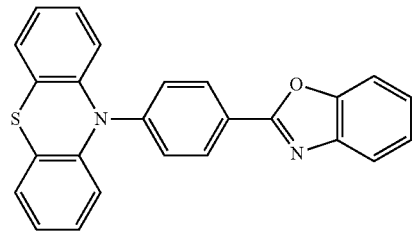
2-22
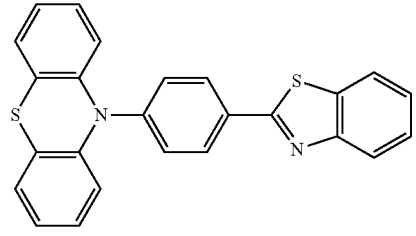

2-23
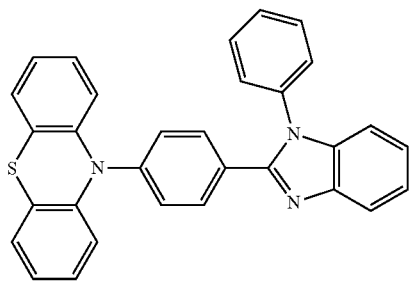
2-24
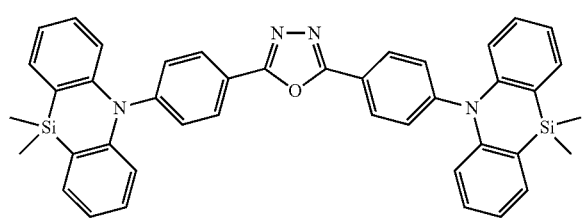
2-25
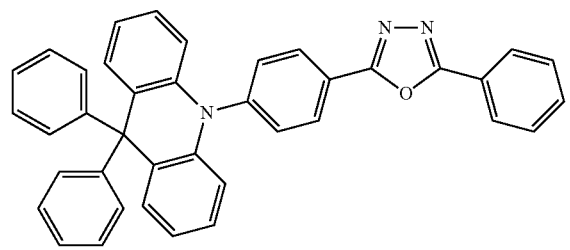
2-26
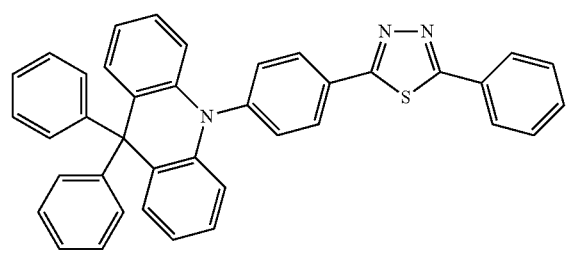
2-27
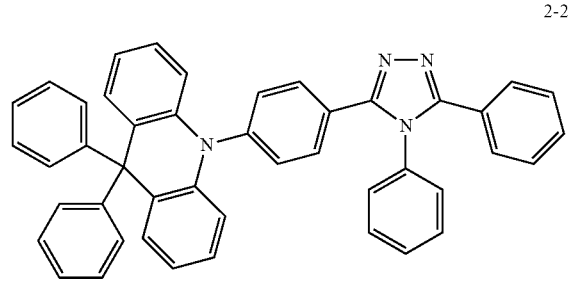
2-28
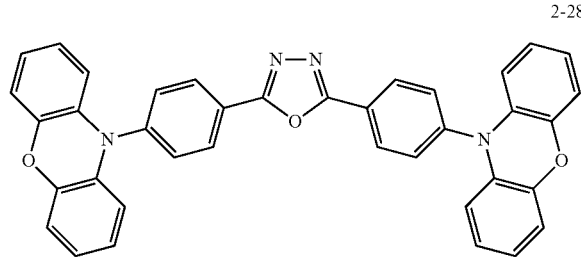
2-29
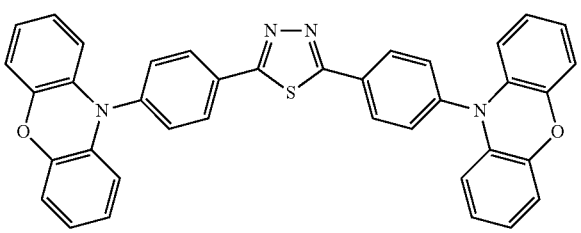
2-30
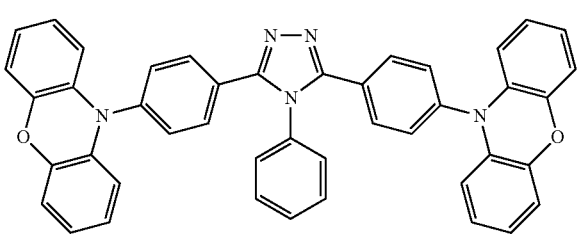
2-31
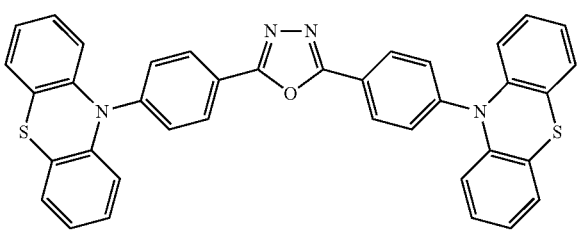
2-32
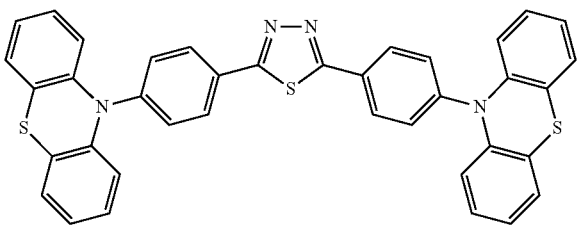
2-33
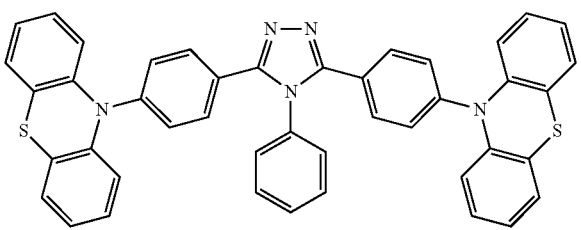
2-34
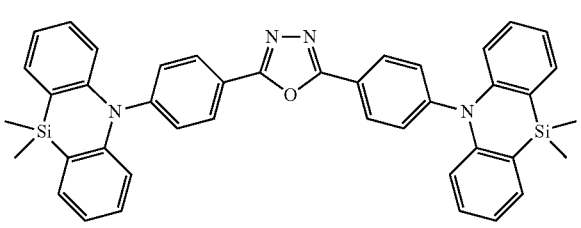

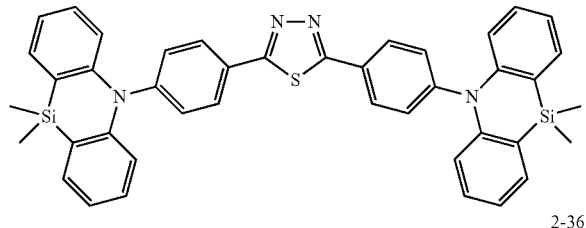

2-35

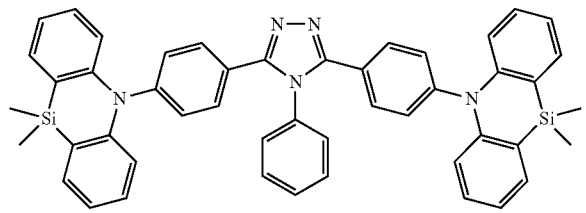

2-36

The emission layer EML may emit light by a luminescence mechanism based on the transition from a singlet state to a ground state. For example, the emission layer EML may emit thermally activated delayed fluorescence (TADF). For example, the organic electroluminescence device 10 according to an embodiment of the present disclosure may be a thermally activated delayed fluorescence device.

The emission layer EML may include a host and a dopant, as described above. If the second heterocyclic compound is the host, a suitable material may be used as the dopant, and if the second heterocyclic compound is the dopant, a suitable material may be used as the host.

In an implementation, the host may include, e.g., tris(8-hydroxyquinolino)aluminum (Alq3), 4,4'-bis(N-carbazolyl)-1,1'-biphenyl (CBP), poly(n-vinylcarbazole) (PVK), 9,10-di(naphthalene-2-yl)anthracene (ADN), 4,4',4"-tris (carbazol-9-yl)-triphenylamine (TCTA), 1,3,5-tris(N-phenylbenzimidazole-2-yl)benzene (TPBi), 3-tert-butyl-9,10-di (naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetra siloxane (DPSiO$_4$), 2,8-bis(diphenylphosphoryl)dibenzofuran (PPF), etc.

In an implementation, the dopant may include, e.g., styryl derivatives (such as 1,4-bis[2-(3-N-ethylcarbazolyl)vinyl] benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalene-2-yl)vinyl)phenyl-N-phenylbenzeneamine (N-BDAVBi)), perylene and the derivatives thereof (such as 2,5,8,11-tetra-t-butylperylene (TBP)), pyrene and the derivatives thereof (such as 1,1-dipyrene, 1,4-dipyrenylbenzene, and 1,4-bis(N,N-diphenylamino)pyrene), 2,5,8,11-tetra-t-butylperylene (TBP), 1,3,5-tris(N-phenylbenzimidazole-2-yl)benzene (TPBi), [bis-(4-(9H-carbazol-9-yl)phenyl)methanone (Cz2BP), etc.

The electron transport region ETR may be provided on the emission layer EML. In an implementation, the electron transport region ETR may include, e.g., at least one of an electron blocking layer, an electron transport layer ETL, or an electron injection layer EIL.

In an implementation, the electron transport region ETR may have a single layer formed using a single material, a single layer formed using a plurality of different materials, or a multilayer structure including a plurality of layers formed using a plurality of different materials.

For example, the electron transport region ETR may have the structure of a single layer such as an electron injection layer EIL and an electron transport layer ETL, or a single layer structure formed using an electron injection material and an electron transport material. In an implementation, the electron transport region ETR may have a single layer structure formed using a plurality of different materials, or a structure laminated one by one from the first electrode EL1 of electron transport layer ETL/electron injection layer EIL, or hole blocking layer/electron transport layer ETL/electron injection layer EIL. The thickness of the electron transport region ETR may be, e.g., from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes the electron transport layer ETL, the electron transport region ETR may include, e.g., tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl)anthracene (ADN), or a mixture thereof. The thickness of the electron transport layer ETL may be from about 100 Å to about 1,000 Å, e.g., from about 150 Å to about 500 Å. If the thickness of the electron transport layer ETL satisfies the above-described range, satisfactory electron transport properties may be obtained without the substantial increase of a driving voltage.

If the electron transport region ETR includes the electron injection layer EIL, the electron transport region ETR may include, e.g., LiF, lithium quinolate (LiQ), Li$_2$O, BaO, NaCl, CsF, a metal in lanthanoides such as Yb, or a metal halide such as RbCl and RbI. In an implementation, the electron injection layer EIL also may be formed using a mixture material of an electron transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate. The thickness of the electron injection layer EIL may be from about 1 Å to about 100 Å, e.g. about 3 Å to about 90 Å. In the case where the thickness of the electron injection layer EIL satisfies the above described range, satisfactory electron injection properties may be obtained without inducing the substantial increase of a driving voltage.

The electron transport region ETR may include a hole blocking layer, as described above. In an implementation, the hole blocking layer may include, e.g., at least one of bis[2-(diphenylphosphino)phenyl]ether oxide (DPEPO), 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 may be a common electrode or a cathode. The second electrode EL2 may be a transmissive electrode, a transflective electrode or a reflective electrode. In the case where the second electrode EL2 is the transmissive electrode, the second electrode EL2 may include a transparent metal oxide, e.g., ITO, IZO, ZnO, ITZO, etc.

In the case where the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials or a transparent conductive layer formed using ITO, IZO, ZnO, ITZO, etc.

In an implementation, the second electrode EL2 may be connected with an auxiliary electrode. If the second electrode EL2 is connected with the auxiliary electrode, the resistance of the second electrode EL2 may be decreased.

In the organic electroluminescence device 10, voltages are applied to each of the first electrode EL1 and the second electrode EL2, and holes injected from the first electrode EL1 move via the hole transport region HTR to the emission layer EML, and electrons injected from the second electrode EL2 move via the electron transport region ETR to the emission layer EML. The electrons and holes are recombined in the emission layer EML to generate excitons, and the excitons may emit light via transition from an excited state to a ground state.

In the case where the organic electroluminescence device 10 is a top emission type, the first electrode EL1 may be a reflective electrode, and the second electrode EL2 may be a transmissive electrode or a transflective electrode. In the case where the organic electroluminescence device 10 is a bottom emission type, the first electrode EL1 may be the transmissive electrode or the transflective electrode, and the second electrode EL2 may be the reflective electrode.

The organic electroluminescence device according to an embodiment of the present disclosure may include, e.g., a compound having a structure derived from acridane (or acridan) commonly in the hole transport region (e.g., a layer contacting the emission layer) and the emission layer, respectively, and thus, HOMO energy may be controlled, thereby improving hole injection properties and attaining high efficiency.

Hereinafter, the present disclosure will be explained more particularly referring to preferred embodiments and comparative embodiments. The following embodiments are only for illustration to assist the understanding of the present disclosure, but the scope of the present disclosure is not limited thereto.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside of the scope of the embodiments. Further, it will be understood that the embodiments are not limited to the particular details described in the Examples and Comparative Examples.

Synthetic Examples

1. Synthesis of Compound 1-1

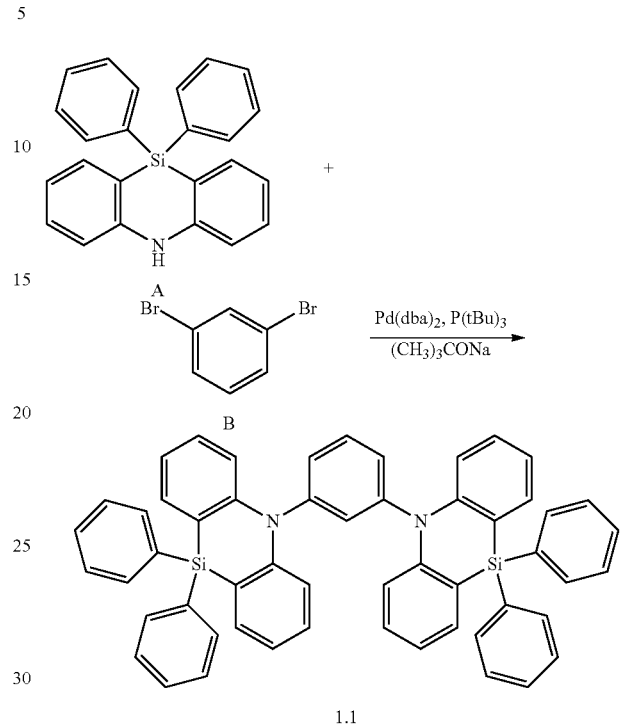

Under an argon atmosphere, to 4.50 g of Compound A, 1.49 g of Compound B, 0.18 g of palladium(0)bis(dibenzylideneacetone) (Pd(dba)$_2$), and 7.42 g of sodium tert-butoxide, 100 ml of toluene and 1.0 ml of a 2 M toluene solution of tri(tert-butyl)phosphine were added in order, followed by heating and refluxing for about 5 hours. The reaction solution cooled to ambient temperature was filtered, and 100 ml of ethanol was added to a filtrate. Precipitated crystal was filtered and washed with 50 ml of water and 100 ml of ethanol in order to obtain 4.4 g (yield 94%) of Compound 1-1 as a lemon yellow powder. The structure of the product was identified by FAB-MS (M/z 772.3 (M+), 773.3 (MH+)).

2. Synthesis of Compound 1-2

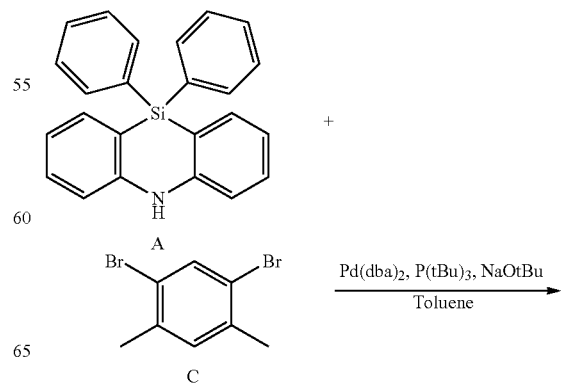

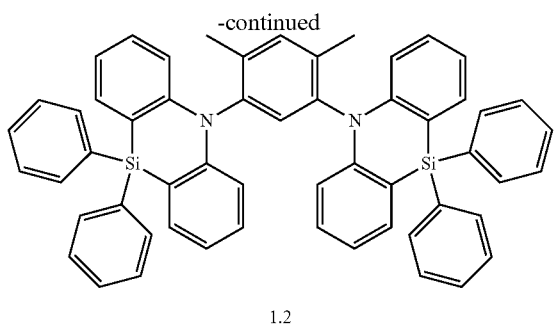

1.2

Under an argon atmosphere, to 4.50 g of Compound A, 1.67 g of Compound C, 0.18 g of palladium(0)bis(dibenzylideneacetone), and 7.42 g of sodium tert-butoxide, 100 ml of toluene and 1.0 ml of a 2 M toluene solution of tri(tert-butyl)phosphine were added in order, followed by heating and refluxing for about 5 hours. The reaction solution cooled to ambient temperature was filtered, and 100 ml of ethanol was added to a filtrate. Precipitated crystal was filtered and washed with 50 ml of water and 100 ml of ethanol in order to obtain 3.44 g (yield 68%) of Compound 1-2 as a lemon yellow powder. The structure of the product was identified by FAB-MS (M/z 800.3 (M+). 801.3 (MH+)).

3. Synthesis of Compound 1-11

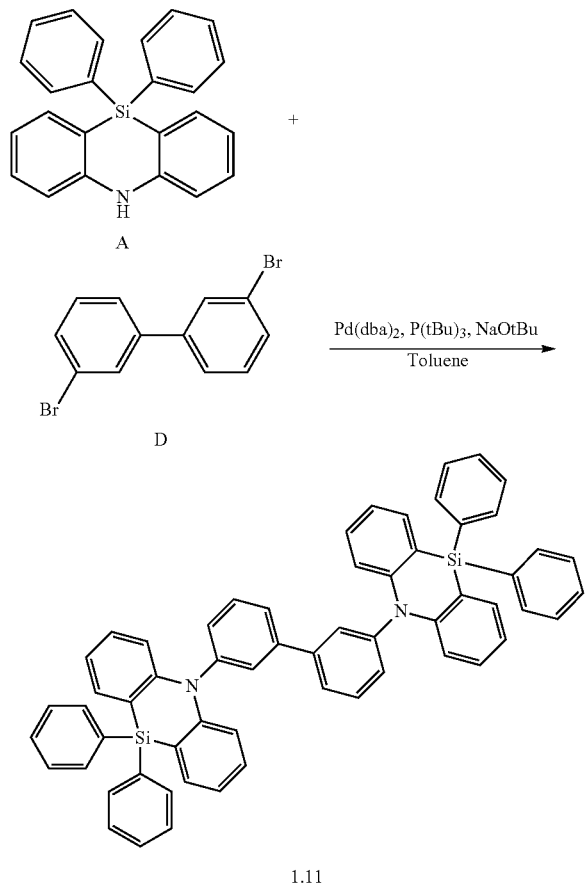

1.11

Under an argon atmosphere, to 4.50 g of Compound A, 1.97 g of Compound D, 0.18 g of palladium(0) bis(dibenzylideneacetone), and 7.42 g of sodium tert-butoxide, 100 ml of toluene and 1.0 ml of a 2 M toluene solution of tri(tert-butyl)phosphine were added in order, followed by heating and refluxing for about 5 hours. The reaction solution cooled to ambient temperature was filtered, and 100 ml of ethanol was added to a filtrate. Precipitated crystal was filtered, washed with 50 ml of water and 100 ml of ethanol in order, and separated by column chromatography (toluene) to obtain 4.90 g (yield 92%) of Compound 1-11 as a lemon yellow powder. The structure of the product was identified by FAB-MS (M/z 848.3 (M+), 849.3 (MH+)).

4. Synthesis of Compound 1-12

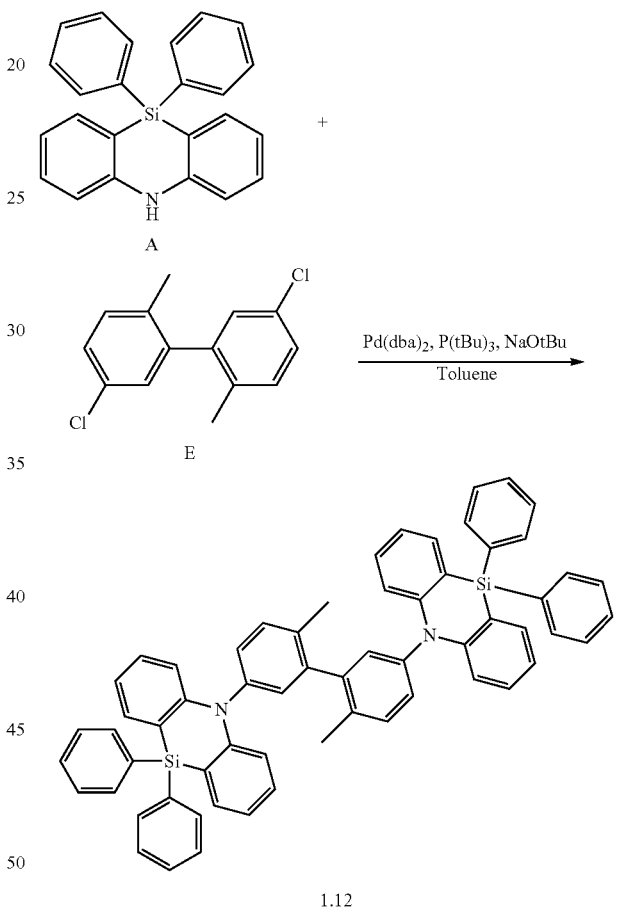

1.12

Under an argon atmosphere, to 4.50 g of Compound A. 1.58 g of Compound E. 0.18 g of palladium(0) bis(dibenzylideneacetone), and 7.42 g of sodium tert-butoxide, 100 ml of toluene and 1.0 ml of a 2 M toluene solution of tri(tert-butyl)phosphine were added in order, followed by heating and refluxing for about 5 hours. The reaction solution cooled to ambient temperature was filtered, and 100 ml of ethanol was added to a filtrate. Precipitated crystal was filtered, washed with 50 ml of water and 100 ml of ethanol in order, and separated by column chromatography (toluene) to obtain 4.8 g (yield 87%) of Compound 1-12 as a lemon yellow powder. The structure of the product was identified by FAB-MS (M/z 876.3 (M+), 877.3 (MH+)).

5. Synthesis of Compound 1-16

Synthesis of Compound F

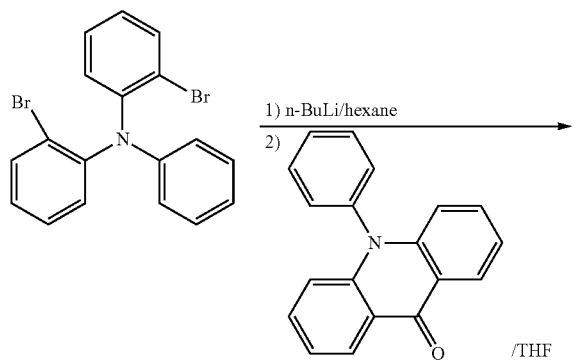

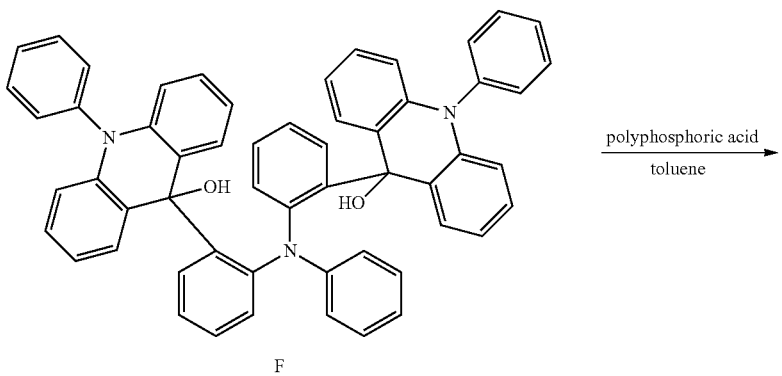

Under an argon (Ar) atmosphere, to 100 ml of a THF solution cooled to about −78° C. and including 4.0 g of 2,2'-dibromo-triphenylamine, 15 ml of a hexane solution including 1.6 mol/L of n-BuLi was added and stirred for about 1 hour. 50 ml of a THF solution including 5.5 g of 10-phenylacridone was added dropwise for about 1 hour while cooling. Then, stirring was performed at ambient temperature for about 6 hours. To the reaction product thus obtained, an aqueous ammonium hydroxide solution was added, residues after concentrating in vacuum were dissolved in methylene chloride, and separation was performed by column chromatography to obtain 5.0 g (yield 64%) of Compound F as a white powder.

Synthesis of Compound 1-16

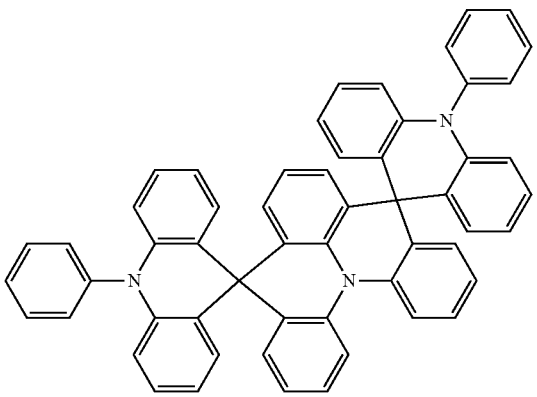

A toluene solution including 5.0 g of Compound F was heated in the presence of polyphosphoric acid at about 60° C. for about 6 hours, and then, cooled. The reaction product was extracted with water-dichloromethane, and residues after concentrating an organic layer under a reduced pressure were separated by column chromatography to obtain 2.4 g (yield 49%) of Compound 1-16 as a white powder. The molecular weight measured by FAB-MS was 751. From the results, the white solid compound was identified as Compound 1-16.

6. Synthesis of Compound 2-2

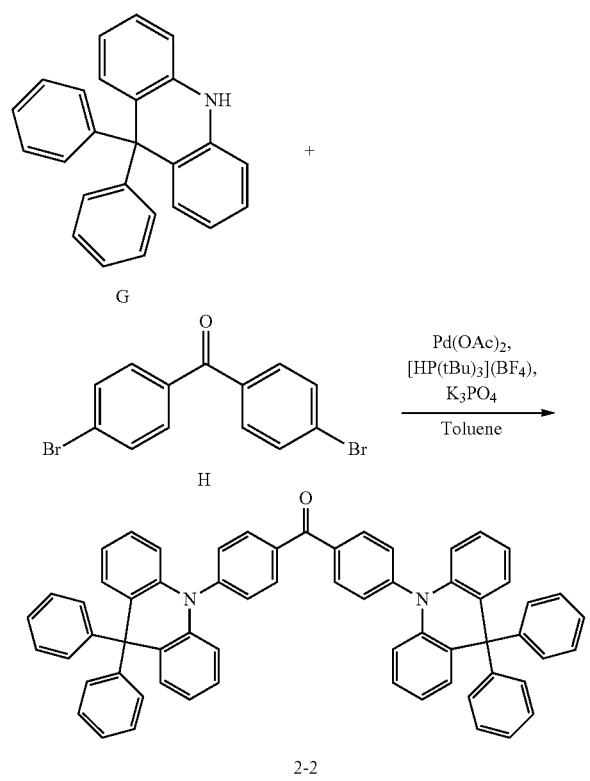

Under an argon atmosphere, to 4.0 g of Compound G, 1.07 g of Compound H, 0.135 g of palladium acetate. 0.52 g of tri-tert-butylphosphonium tetrafluoroborate, and 10.2 g of potassium phosphate, 100 ml of toluene was added and heated and refluxed for about 5 hours. The reaction solution cooled to ambient temperature was filtered, and 100 ml of ethanol was added to a filtrate. Precipitated crystal was filtered, washed with 50 ml of water and 100 ml of ethanol in order, and separated by column chromatography (toluene) to obtain 4.0 g (yield 80%) of Compound 2-2 as a lemon yellow powder. The structure of the product was identified by FAB-MS (M/z 844.3 (M+), 845.3 (MH+)).

(Device Manufacturing Examples)

Organic electroluminescence devices of Examples 1 to 6 and Comparative Examples 1 and 4 were manufactured as follows. A first electrode with a thickness of about 150 nm was formed using ITO, a hole injection layer with a thickness of about 10 nm was formed using HAT-CN, a hole transport layer with a thickness of about 80 nm was formed using α-NPD, an electron blocking layer with a thickness of about 5 nm was formed using the Example compound or Comparative compound listed in Table 1 below, an emission layer with a thickness of about 20 nm was formed using the Example compound or Comparative compound listed in Table 1 below, a hole blocking layer with a thickness of about 10 nm was formed using DPEPO, an electron transport layer with a thickness of about 30 nm was formed using TPBi, an electron injection layer with a thickness of about 0.5 nm was formed using LiF, and a second electrode with a thickness of about 100 nm was formed using Al. Each layer was formed by a vacuum deposition method.

Then, an inception voltage and external quantum efficiency of the organic electroluminescence devices thus manufactured were measured. The external quantum efficiency was measured using a brightness light distribution characteristics measurement system of C9920-12 manufactured by HAMAMATSU Photonics Co. The evaluation results are shown in Table 1 below.

TABLE 1

|  | Electron blocking layer material | Emission layer dopant material (18%) | Emission layer host material | Inception voltage (V, 10 mA/cm$^2$) | External quantum efficiency (%) |
| --- | --- | --- | --- | --- | --- |
| Example 1 | Compound 1-1 | Compound 2-1 | DPEPO | 6.2 | 18.1 |
| Example 2 | Compound 1-2 | Compound 2-1 | DPEPO | 6.4 | 18.5 |
| Example 3 | Compound 1-3 | Compound 2-1 | DPEPO | 6.1 | 16.7 |
| Example 4 | Compound 1-2 | Cz2BP | Compound 1-2 | 6.2 | 16.5 |
| Example 5 | Compound 1-2 | Compound 2-2 | DPEPO | 6.0 | 17.5 |
| Example 6 | Compound 1-3 | Compound 2-2 | DPEPO | 5.9 | 17.3 |
| Comparative Example 1 | mCP | Compound 2-1 | DPEPO | 6.6 | 15.0 |
| Comparative Example 2 | Compound 1-1 | Cz2BP | DPEPO | 8.0 | 6.0 |
| Comparative Example 3 | Compound 2-1 | Cz2BP | DPEPO | 5.6 | 4.0 |
| Comparative Example 4 | mCP | Cz2BP | DPEPO | 6.8 | 13.0 |

TABLE 1-continued

| Electron blocking layer material | Emission layer dopant material (18%) | Emission layer host material | Inception voltage (V, 10 mA/cm$^2$) | External quantum efficiency (%) |
|---|---|---|---|---|

DPEPO mCP

Cz2BP

Compound 1-3 was synthesized by a method disclosed in KR 2011-120075 (Spiro compound as an electroluminescent material for organic electroluminescent element, SFC Ltd.), and Compound 2-1 was synthesized by a method disclosed in Journal of Display Technology, 5(6), 236-240; 2009.

From the results in Table 1, it may be seen that the organic electroluminescence device according to the Examples attained high efficiency. When comparing Examples 1 to 6 with Comparative Examples 1 to 4, it may be seen that the emission efficiency of the organic electroluminescence device according to the Examples was improved. The results are thought to be attained as shown in Table 2 below by controlling HOMO energy and improving hole injection properties, by using a compound having a relatively high lowest triplet excitation energy as a material of an electron blocking layer and by commonly including a structure derived from acridane in the materials of an electron blocking layer and an emission layer. In addition, by including 2 structures derived from acridane in the material of the electron blocking layer, the hole mobility of the electron blocking layer was increased, thereby decreasing an inception voltage.

TABLE 2

|  | HOMO energy (eV) | The lowest triplet excitation energy T1 (eV) | HOMO energy difference from Compound 2-1 (eV) |
|---|---|---|---|
| Compound 1-1 | −5.18 | 3.30 | 0.06 |
| Compound 1-2 | −5.15 | 3.27 | 0.03 |
| Compound 1-3 | −4.86 | 3.15 | 0.26 |
| mCP | −5.45 | 3.18 | 0.33 |
| Compound 2-1 | −5.12 | 2.82 | — |
| Compound 2-2 | −5.22 | 2.92 | — |

The lowest triplet excitation energy was calculated using TD-B3LYP/631-G(d) by theoretical chemistry simulation software Gaussian 09.

The organic electroluminescence device according to an embodiment of the present disclosure may attain improved efficiency.

The organic electroluminescence device according to an embodiment of the present disclosure has excellent efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made

What is claimed is:
1. An organic electroluminescence device, comprising:
a first electrode;
a hole transport region on the first electrode, the hole transport region including:
a hole injection layer on the first electrode;
a hole transport layer on the hole injection layer; and
an electron blocking layer on the hole transport layer;
an emission layer on the hole transport region;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof,
wherein the emission layer includes a second heterocyclic compound represented by Formula 4 as a dopant, and the electron blocking layer includes a first heterocyclic compound represented by the following Formula 2-1, and does not include the second heterocyclic compound:

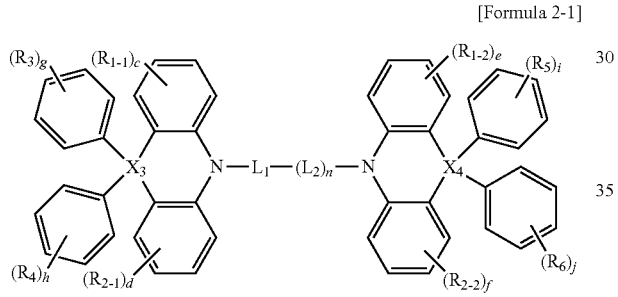

[Formula 2-1]

wherein, in Formula 2-1,
$L_1$ is a substituted phenylene group, a substituted divalent biphenyl group, or a substituted or unsubstituted fluorenylene group, and $L_2$ is a substituted or unsubstituted arylene group having 6 to 30 ring carbon atoms, wherein the substituents of $L_1$ and $L_2$ are each independently selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocycle, provided that the substituent of $L_1$ does not form a ring with an adjacent group, and the substituent of $L_2$ does not form a ring with an adjacent group,
"n" is 0 or 1,
$R_{1-1}$, $R_{1-2}$, $R_{2-1}$, and $R_{2-2}$ are each independently a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms,
$R_{1-1}$, $R_{1-2}$, $R_{2-1}$, and $R_{2-2}$ are separate or combined with an adjacent group to form a ring,
"c" to "f" are each independently an integer of 0 to 4,
$X_3$ and $X_4$ are each independently Si,
$R_3$ to $R_6$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and
"g" to "j" are each independently an integer of 0 to 5,

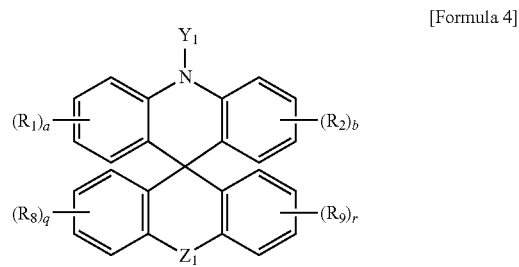

[Formula 4]

and
wherein, in Formula 4,
$Z_1$ is —CO—, or —SO$_2$—,
$R_8$ is a hydrogen atom, a deuterium atom, an alkyl group having 1 to 20 carbon atoms, an aryl group having 6 to 30 ring carbon atoms,
a thiophenyl group, a furanyl group, a pyrrolyl group, an indolyl group, a carbazolyl group, an N-arylcarbazolyl group, an N-heteroaryl carbazolyl group, an N-alkyl carbazolyl group, a benzocarbazole group, a benzothiophenyl group, a benzofuranyl group, a thienothiophene group, a phenoxazinyl group, a phenothiazinyl group, a dibenzosilole group, a dibenzothiophenyl group, or a dibenzofuranyl group, each being unsubstituted or substituted with at least one substituent selected from the group consisting of a deuterium atom, an amino group, a silyl group, a boron group, an alkyl group, an alkenyl group, or an aryl group;
$R_9$ is a deuterium atom, an alkyl group having 1 to 20 carbon atoms, an aryl group having 6 to 30 ring carbon atoms,
a thiophenyl group, a furanyl group, a pyrrolyl group, an indolyl group, a carbazolyl group, an N-arylcarbazolyl group, an N-heteroaryl carbazolyl group, an N-alkyl carbazolyl group, a benzocarbazole group, a benzothiophenyl group, a benzofuranyl group, a thienothiophene group, a phenoxazinyl group, a phenothiazinyl group, a dibenzosilole group, a dibenzothiophenyl group, or a dibenzofuranyl group, each being unsubstituted or substituted with at least one substituent selected from the group consisting of a deuterium atom, an amino group, a silyl group, a boron group, an alkyl group, an alkenyl group, or an aryl group;
"q" and "r" are each independently an integer of 1 to 4,
$Y_1$ is a hydrogen atom, a deuterium atom, a substituted or unsubstituted alkyl group having 2 to 20 carbon atoms, a substituted or unsubstituted naphthyl, fluorenyl, anthracenyl, phenanthryl, quaterphenyl, quinquephenyl, sexiphenyl, biphenylene, triphenylene, pyrenyl, benzofluoranthenyl, or chrysenyl group, or a substituted or unsubstituted thiophene, furan, pyrrole, imidazole, thiazole, oxazole, oxadiazole, triazole, bipyridyl, pyrimidyl, triazole, acridyl, pyridazine, pyrazinyl, phenoxazinyl, phthalazinyl, pyrido pyrimidinyl, pyrido pyrazinyl, pyrazino pyrazinyl, indole, carbazole, N-arylcarbazole, N-heteroaryl carbazole, N-alkyl carbazole, benzoxazole, benzimidazole, benzothiazole, benzocarbazole, benzothiophene, dibenzothiophenyl, thienothiophene, benzofuranyl, phenanthroline, thiazolyl, isoxazolyl, oxadiazolyl, thiadiazolyl, benzothiazolyl, phenothiazinyl, dibenzosilole, or dibenzofuranyl group, $R_1$ and $R_2$ are each independently a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_1$ and $R_2$ are separate or combined with an adjacent group to form a ring, and "a" and "b" are each independently an integer of 0 to 4.

2. The organic electroluminescence device as claimed in claim 1, wherein $R_{1-1}$ and $R_{1-2}$ are the same, $R_{2-1}$ and $R_{2-2}$ are the same, "c" and "e" are the same, and "d" and "f" are the same.

3. The organic electroluminescence device as claimed in claim 1, wherein $Z_1$ is —CO—.

4. The organic electroluminescence device as claimed in claim 1, wherein:
the hole transport region has a multilayer structure, and
a layer that directly contacts the emission layer in the multilayer structure includes the first heterocyclic compound.

5. The organic electroluminescence device as claimed in claim 1, wherein the emission layer is to emit light by a luminescence mechanism based on the transition from a singlet state to a ground state.

6. The organic electroluminescence device as claimed in claim 5, wherein the emission layer is to emit thermally activated delayed fluorescence.

7. The organic electroluminescence device as claimed in claim 1, wherein the first heterocyclic compound is a compound of the following Compound Group 1:

[Compound Group 1]

1-2
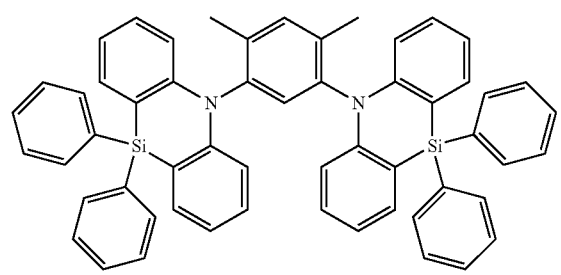

1-4
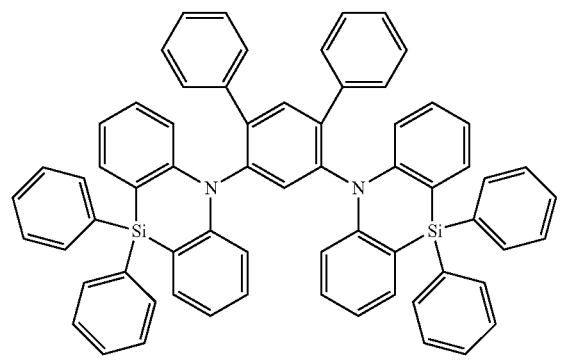

1-5
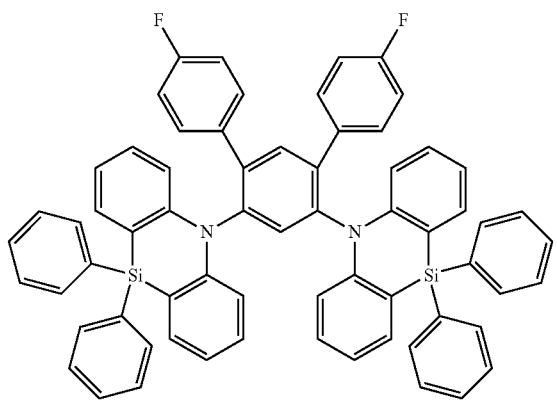

1-7
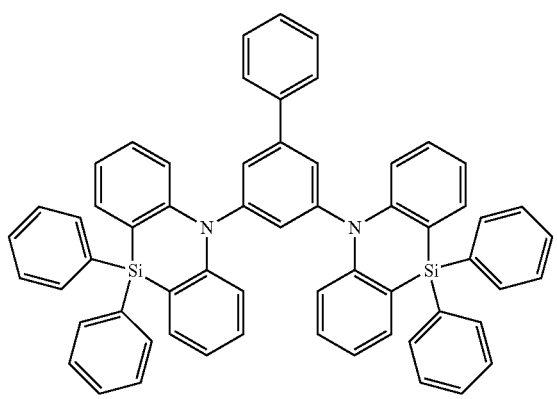

1-12
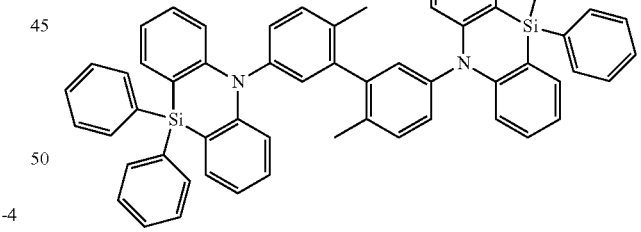

1-13
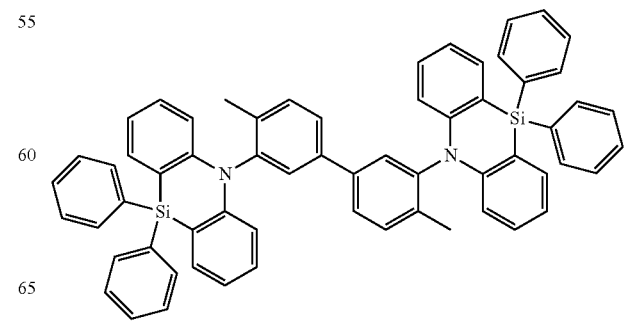

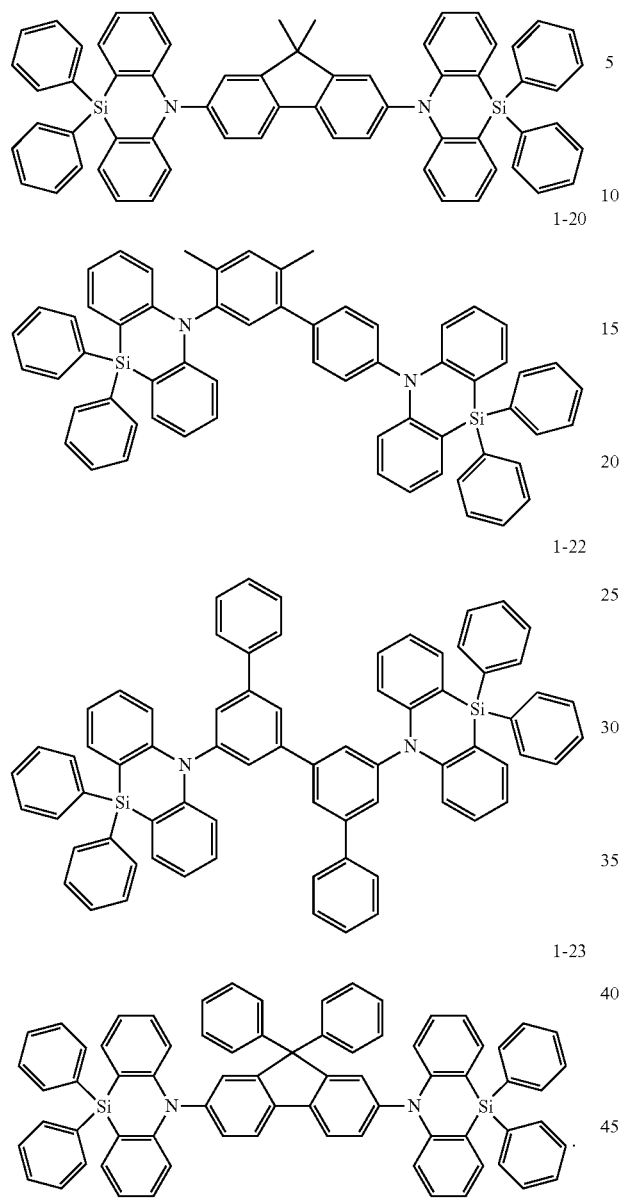

8. An organic electroluminescence device, comprising:
a first electrode;
a hole transport region on the first electrode, the hole transport region including:
  a hole injection layer on the first electrode;
  a hole transport layer on the hole injection layer; and
  an electron blocking layer on the hole transport layer;
an emission layer on the hole transport region;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof,
wherein the emission layer includes a second heterocyclic compound represented by Formula 4 as a dopant, and the electron blocking layer includes a first heterocyclic compound represented by the following Formula 2-1, and does not include the second heterocyclic compound:

[Formula 2-1]

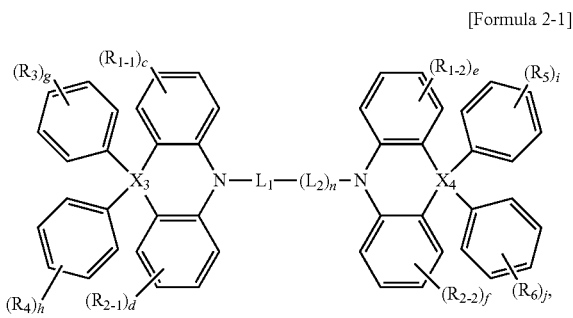

wherein, in Formula 2-1,
L₁ and L₂ are each independently a substituted or unsubstituted arylene group having 6 to 30 ring carbon atoms,
"n" is 0 or 1,
$R_{1-1}$, $R_{1-2}$, $R_{2-1}$, and $R_{2-2}$ are each independently a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms,
$R_{1-1}$, $R_{1-2}$, $R_{2-1}$, and $R_{2-2}$ are separate or combined with an adjacent group to form a ring,
"c" to "f" are each independently an integer of 0 to 4,
$X_3$ and $X_4$ are each independently Si,
$R_3$ to $R_6$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and
"g" to "j" are each independently an integer of 0 to 5,

[Formula 4]

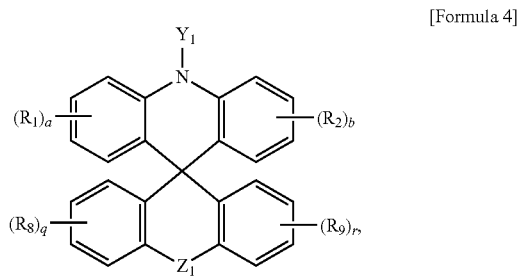

and
wherein, in Formula 4,
$Z_1$ is —SO₂—,
$R_8$ is a hydrogen atom, a deuterium atom, an alkyl group having 1 to 20 carbon atoms, an aryl group having 6 to 30 ring carbon atoms,
a thiophenyl group, a furanyl group, a pyrrolyl group, an indolyl group, a carbazolyl group, an N-arylcarbazolyl group, an N-heteroaryl carbazolyl group, an N-alkyl carbazolyl group, a benzocarbazole group, a benzothiophenyl group, a benzofuranyl group, a thienothiophene group, a phenoxazinyl group, a phenothiazinyl group, a dibenzosilole group, a dibenzothiophenyl group, or a dibenzofuranyl group, each being unsubstituted or substituted with at least one substituent selected from the group consisting of a deuterium atom, an amino group, a silyl group, a boron group, an alkyl group, an alkenyl group, or an aryl group;

$R_9$ is a deuterium atom, an alkyl group having 1 to 20 carbon atoms, an aryl group having 6 to 30 ring carbon atoms, a thiophenyl group, a furanyl group, a pyrrolyl group, an indolyl group, a carbazolyl group, an N-arylcarbazolyl group, an N-heteroaryl carbazolyl group, an N-alkyl carbazolyl group, a benzocarbazole group, a benzothiophenyl group, a benzofuranyl group, a thienothiophene group, a phenoxazinyl group, a phenothiazinyl group, a dibenzosilole group, a dibenzothiophenyl group, or a dibenzofuranyl group, each being unsubstituted or substituted with at least one substituent selected from the group consisting of a deuterium atom, an amino group, a silyl group, a boron group, an alkyl group, an alkenyl group, or an aryl group;

"q" and "r" are each independently an integer of 1 to 4, $Y_1$ is a hydrogen atom, a deuterium atom, a substituted or unsubstituted alkyl group having 2 to 20 carbon atoms, a substituted or unsubstituted naphthyl, fluorenyl, anthracenyl, phenanthryl, quaterphenyl, quinquephenyl, sexiphenyl, biphenylene, triphenylene, pyrenyl, benzofluoranthenyl, or chrysenyl group, or a substituted or unsubstituted thiophene, furan, pyrrole, imidazole, thiazole, oxazole, oxadiazole, triazole, bipyridyl, pyrimidyl, triazole, acridyl, pyridazine, pyrazinyl, phenoxazinyl, phthalazinyl, pyrido pyrimidinyl, pyrido pyrazinyl, pyrazino pyrazinyl, indole, carbazole, N-arylcarbazole, N-heteroaryl carbazole, N-alkyl carbazole, benzoxazole, benzimidazole, benzothiazole, benzocarbazole, benzothiophene, dibenzothiophenyl, thienothiophene, benzofuranyl, phenanthroline, thiazolyl, isoxazolyl, oxadiazolyl, thiadiazolyl, benzothiazolyl, phenothiazinyl, dibenzosilole, or dibenzofuranyl group, $R_1$ and $R_2$ are each independently a hydrogen atom, a deuterium atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_1$ and $R_2$ are separate or combined with an adjacent group to form a ring, and "a" and "b" are each independently an integer of 0 to 4.

* * * * *